(12) United States Patent
Miyoshi et al.

(10) Patent No.: US 11,000,477 B2
(45) Date of Patent: May 11, 2021

(54) PREPARING METHOD FOR POSITIVELY-ELECTRIFIED CHARGED NIOSOME, AND CHARGED NIOSOME

(71) Applicant: J-Network, Inc., Huntington Beach, CA (US)

(72) Inventors: Tatsuro Miyoshi, Huntington Beach, CA (US); Brian Charles Keller, Huntington Beach, CA (US); Akira Kodama, Huntington Beach, CA (US)

(73) Assignee: J-NETWORK, INC., Huntington Beach, CA (US)

( * ) Notice: Subject to any disclaimer, the term of this patent is extended or adjusted under 35 U.S.C. 154(b) by 0 days.

(21) Appl. No.: 16/040,725

(22) Filed: Jul. 20, 2018

(65) Prior Publication Data

US 2019/0091153 A1    Mar. 28, 2019

(30) Foreign Application Priority Data

Sep. 25, 2017    (JP) .............................. JP2017-183924

(51) Int. Cl.
*A61K 9/127*    (2006.01)
*A61K 8/14*    (2006.01)
(Continued)

(52) U.S. Cl.
CPC ............ *A61K 9/1277* (2013.01); *A61K 8/042* (2013.01); *A61K 8/14* (2013.01); *A61K 8/676* (2013.01);
(Continued)

(58) Field of Classification Search
CPC ...... A61K 9/1277; A61K 8/86; A61K 9/1271; A61K 8/042; A61K 8/676; A61K 9/0014;
(Continued)

(56) References Cited

U.S. PATENT DOCUMENTS 5,156,766 A * 10/1992 Behan ...................... A61K 8/06
424/450
6,958,160 B1 * 10/2005 Keller .................. A61K 9/1271
264/4.1
(Continued)

FOREIGN PATENT DOCUMENTS

JP        4497765       7/2002
WO    2012161198    11/2012

OTHER PUBLICATIONS

Uster, P.S., et al in FEBS Letters, 386, pp. 243-246, 1996.*
(Continued)

*Primary Examiner* — Gollamudi S Kishore
(74) *Attorney, Agent, or Firm* — Shlesinger, Arkwright & Garvey LLP

(57) ABSTRACT

To provide a preparing method for a charged niosome which is formed of a lipid containing a diacylglycerol PEG adduct and which is capable of being excellently impregnated into the skin and stored in the skin. The preparing method for the charged niosome includes the steps of: preparing a suspension of a niosome by mixing a lipid containing a diacylglycerol PEG adduct with an aqueous solution at a temperature where the lipid is in a liquid state so that the lipid forms the niosome spontaneously; preparing a cationic-surfactant aqueous solution by mixing a cationic surfactant with an acidic aqueous solution, the cationic surfactant being chosen from a group which consists of an aliphatic amine, an aliphatic or aliphatic-amide quaternary ammonium salt, an aliphatic amideamine and an acylamino acid derivative, the hydrophobic part of the cationic surfactant containing a saturated or unsaturated normal hydrocarbon group having a carbon number of 11 to 21; and preparing a suspension of a charged niosome by mixing the suspension of the niosome with the cationic-surfactant aqueous solution and allowing (Continued)

the cationic surfactant to modify a surface of the niosome with a positive charge of the hydrophilic part of the cationic surfactant.

3 Claims, 10 Drawing Sheets

(51) Int. Cl.
| | |
|---|---|
| *A61Q 19/00* | (2006.01) |
| *A61K 8/86* | (2006.01) |
| *A61K 8/04* | (2006.01) |
| *A61K 8/67* | (2006.01) |
| *A61K 9/00* | (2006.01) |
| *A61K 9/06* | (2006.01) |
| *A61K 31/375* | (2006.01) |
| *B82Y 5/00* | (2011.01) |

(52) U.S. Cl.
CPC .............. *A61K 8/86* (2013.01); *A61K 9/0014* (2013.01); *A61K 9/06* (2013.01); *A61K 9/1271* (2013.01); *A61K 9/1272* (2013.01); *A61K 31/375* (2013.01); *A61Q 19/00* (2013.01); *B82Y 5/00* (2013.01)

(58) Field of Classification Search
CPC ...... A61K 9/06; A61K 31/375; A61K 9/1272; A61K 8/14; A61K 8/365; A61K 8/41; A61K 8/416; A61K 8/42; A61K 8/44; A61K 47/12; A61K 47/14; A61K 47/18; A61K 47/183; A61K 47/186; A61K 2800/542; A61K 2800/10; A61Q 19/00; B82Y 5/00

See application file for complete search history.

(56) References Cited

U.S. PATENT DOCUMENTS

| | | | |
|---|---|---|---|
| 7,718,190 B2 * | 5/2010 | Keller | A61K 9/1271 264/4.1 |
| 2004/0062780 A1 | 4/2004 | Keller | |
| 2004/0265393 A1 * | 12/2004 | Unger | A61B 17/22004 424/600 |
| 2007/0110798 A1 * | 5/2007 | Drummond | A61K 9/0019 424/450 |
| 2014/0341979 A1 * | 11/2014 | Tamanoi | C07D 207/20 424/450 |
| 2016/0184228 A1 * | 6/2016 | Morrison | A61K 31/616 424/450 |

OTHER PUBLICATIONS

Marianecci, C., et al in Advances in Colloid and interface Science, 205, pp. 187-206, 2014.*

Enhanced Delivery of Retinoic Acid to Skin by Cationic Liposomes, Chem. Pharm. Bull. 54(2) 242-244 (2006).

Effect of Charged and Non-ionic Membrane Additives on Physicochemical Properties and Stability of Niosomes, AAPS PharmSciTech, vol. 9, No. 3, 851-859 (2008).

* cited by examiner

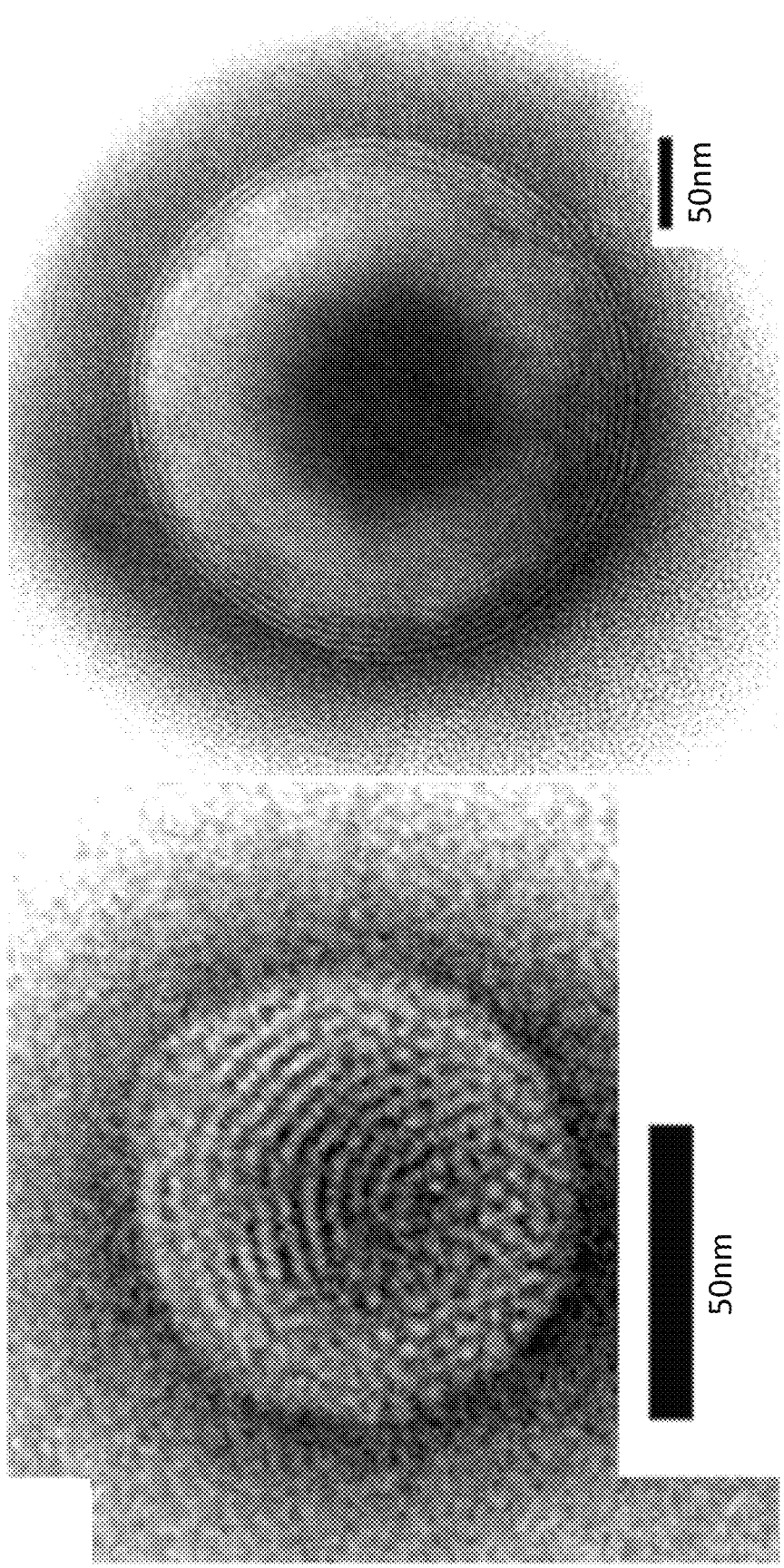

PREPARING METHOD FOR POSITIVELY-ELECTRIFIED CHARGED NIOSOME, AND CHARGED NIOSOME

TECHNICAL FIELD

The present invention relates to a preparing method for a niosome capable of being excellently impregnated into the skin and stored in the skin.

BACKGROUND ART

A liposome is a phospholipid forming a biomembrane or a lipid similar thereto and has the structure of a double membrane or a multiple membrane, the liposome being known as a self-closed colloidal particle having a size of tens of nanometers to hundreds of nanometers. Particularly, a self-closed colloidal particle prepared with a lipid of a non-ionic surfactant is called a niosome. A liposome or a niosome has been widely utilized for drug delivery or the like in the fields of medicaments, cosmetics and the like.

An objective substance such as a medicine can be encapsulated in a water phase inside of a liposome, encapsulated in a membrane of a liposome and bonded on a surface of a liposome. A general method for preparing a liposome includes treatment processes, such as dissolving a lipid with an organic solvent, removing an organic solvent, an ultrasonic treatment or extrusion, and homogenization. In forming a liposome and simultaneously encapsulating a medicine or the like, subsequent treatments may cause the lipid and the medicine to dissolve. Further, problems may arise in the general preparing method, such as making unstable the size of each liposome or the number of liposomes, and on a manufacturing scale, making sterilization more difficult and causing differences in quality between batches.

In order to solve the problems, Patent Document 1 presents a preparing method for forming a liposome spontaneously by mixing a lipid mainly containing a diacylglycerol polyethylene glycol adduct (hereinafter, called the "diacylglycerol PEG adduct") and an aqueous solution containing an objective substance. (In a narrow sense, a self-closed colloidal particle formed of a phospholipid is frequently called a liposome. However, in Patent Document 1, it is formed of a lipid other than a phospholipid and hence called a liposome in a broad sense. Herein, a liposome formed mainly of a lipid other than a phospholipid is called a "niosome".)

In addition, Patent Document 2 includes modifying a surface of a liposome with polyethylene glycol, and thereby, the hydration and steric hindrance of polyethylene glycol enable the liposome to be impregnated into the organism without being captured by the reticulo-endothelial system. Particularly, it is known that the liposome is quite excellently stored in the blood.

In Patent Document 1, the lipid itself equivalent to the diacylglycerol PEG adduct has a PEG chain, and the surface of the liposome formed of the lipid is covered with the PEG chain. Therefore, the liposome of Patent Document 1 is capable of being excellently impregnated into the organism and stably kept in the blood. Hence, this liposome has the same advantages as those of the liposome of Patent Document 1 having the surface modified with polyethylene glycol.

RELATED ART DOCUMENTS

Patent Documents

Patent Document 1: Japanese Patent Publication No. 4497765

Patent Document 2: International Publication No. 2012/161196

SUMMARY OF THE INVENTION

Problems to be Solved by the Invention

The liposome of Patent Document 1 is covered with the PEG chain, and thereby, can be excellently impregnated into the skin. However, this liposome cannot be stored for a long time in the skin, especially in the horn, and because of the inadequate storage time, the liposome is unsuitable for products such as cosmetics.

It is an object of the present invention to provide a preparing method for a niosome which is formed of a lipid mainly containing a diacylglycerol PEG adduct and which is capable of being excellently impregnated into the skin and stored in the skin. It is another object thereof to provide the niosome.

Means for Solving the Problems

In order to accomplish the objects, the present invention provides the follow configurations.

An aspect of the present invention is a preparing method for a positively-electrified charged niosome, including the steps of:

preparing a suspension of a niosome by mixing a lipid containing at least a diacylglycerol PEG adduct with a, specified aqueous solution at a temperature where the lipid is in a liquid state so that the lipid forms the niosome spontaneously;

preparing a cationic-surfactant aqueous solution by mixing a cationic surfactant with an acidic aqueous solution, the cationic surfactant being one or a plurality of cationic surfactants chosen from a group which consists of an aliphatic amine, an aliphatic or aliphatic-amide quaternary ammonium salt, an aliphatic amideamine and an acylamino acid derivative, the hydrophobic part of the cationic surfactant containing a saturated or unsaturated normal hydrocarbon group having a carbon number of 11 to 21; and preparing a suspension of a charged niosome by mixing the suspension of the niosome with the cationic-surfactant aqueous solution and allowing the cationic surfactant to modify a surface of the niosome with a positive charge of the hydrophilic part of the cationic surfactant, wherein the diacylglycerol PEG adduct is one or a plurality chosen from a group which consists of glycerol PEG dioleate-12, glycerol PEG dimyristate-12, glycerol PEG dipalmitate-23, glycerol PEG distearate-12 and glycerol PEG distearate-23.

In the aspect:

the aliphatic amine equivalent to the cationic surfactant is one or a plurality chosen from a group which consists of tetradecylamine, palmitylamine, stearylamine, oleylamine, linoleylamine, behenylamine, N,N-dimethyldodecylamine and N,N-dimethyl-n-octadecylamine;

the aliphatic or aliphatic-amide quaternary ammonium salt equivalent to the cationic surfactant is one or a plurality chosen from a group which consists of tetradecyltrimethyl ammonium chloride, cetyltrimethyl ammonium chloride, stearyltrimethyl ammonium chloride, behenyltrimethyl ammonium chloride and palmitamidopropyltrimethyl ammonium chloride;

the aliphatic amideamine equivalent to the cationic surfactant is one or a plurality chosen from a group which consists of diethylaminoethylamide myristate, dimethylaminoethylamide myristate, dimethylaminopropylamide myristate, dimethylaminopropylamide myristate, diethylaminoethylamide palmitate, dimethylaminoethylamide palmitate, dimethylaminopropylamide palmitate, diethylaminopropylamide palmitate, diethylaminoethylamide stearate, dimethylaminoethylamide stearate, dimethylaminopropylamide stearate, diethylaminopropylamide stearate, diethylaminoethylamide behenate, dimethylaminoethylamide behenate, dimethylaminopropylamide behenate and diethylaminopropylamide behenate; and the acylamino acid derivative equivalent to the cationic surfactant is a cocoylarginineethyl PCA.

In the aspect, the acidic aqueous solution for preparing the cationic-surfactant aqueous solution is equal to, or less than, pH4.

Another aspect of the present invention is a positively-electrified charged niosome, comprising:

a niosome which includes as a constituent thereof a lipid containing at least one or a plurality of diacylglycerol PEG adducts chosen from a group which consists of glycerol PEG dioleate-12, glycerol PEG dimyristate-12, glycerol PEG dipalmitate-23, glycerol PEG distearate-12 and glycerol PEG distearate-23, and encapsulates a specified aqueous solution; and a cationic surfactant modifying a surface of the niosome with a positive charge of the hydrophilic part of the cationic surfactant, wherein the cationic surfactant is one or a plurality of cationic surfactants chosen from a group which consists of an aliphatic amine, an aliphatic amideamine and an acylamino acid derivative, and the hydrophobic part of the cationic surfactant contains one saturated or unsaturated normal hydrocarbon group having a carbon number of 11 to 21.

In addition, a charged-niosome containing product which contains the charged niosome according to this aspect is a lotion preparation, a milky lotion preparation, a gel preparation or a cream preparation.

Advantages of the Invention

The charged niosome according to the present invention is positively electrified and hence is easily absorbed into a negatively-electrified skin surface layer, especially a horny layer. As a result, the charged niosome can be impregnated quite excellently into the horny layer and stored over a longer period of time therein, as compared with an unelectrified niosome.

BRIEF DESCRIPTION OF THE DRAWINGS

FIG. 1A shows the structure of a diacylglycerol PEG adduct equivalent to a main lipid used in the first step and FIGS. 1B-1E show the structure of each example of a cationic surfactant used in the second step.

FIGS. 4A-4B are photomicrographs taken through a transmission electron microscope (TEM) in Working Example 1 and Comparative Example 1 respectively.

FIG. 9A shows test results for the percutaneous absorption in the respective examples and FIG. 9B shows test results for the skin-whitening effect of arbutin as a skin-whitening agent by measuring the luminosity of cells in the respective examples.

MODE FOR CARRYING OUT THE INVENTION

An embodiment of the present invention will be below described with reference to the drawings.

The term "niosome" is generally used as the meaning of a vesicle (a self-closed colloidal particle having a double membrane) by a non-ionic surfactant. However, it herein includes a self-closed colloidal particle having not only a double membrane but also a multiple membrane.

[1] Basic Formation of the Preparing Method

The niosome obtained by the preparing method according to the present invention is a niosome positively electrified in a suspension (hereinafter, called the "charged niosome"). If the simple term "niosome" is below described, that means an uncharged one. The preparing method for the charged niosome according to the present invention basically includes the following three steps. The first step and the second step are not necessarily taken temporally in this order, and hence, can be carried out in parallel or in the reversed order. The third step is the final step carried out by using both a product in the first step and a product in the second step.

The first step: a step of preparing a suspension of a niosome by mixing a lipid containing at least a diacylglycerol PEG adduct with a specified aqueous solution at a temperature where the lipid is in a liquid state so that the lipid forms the niosome spontaneously.

The second step: a step of preparing a cationic-surfactant aqueous solution by mixing a cationic surfactant with an acidic aqueous solution, the cationic surfactant being one or a plurality of cationic surfactants chosen from a group which consists of an aliphatic amine, an aliphatic quaternary ammonium salt, aliphatic-amide quaternary ammonium salt, an aliphatic amideamine and an acylamino acid derivative, the hydrophobic part of the cationic surfactant containing a saturated or unsaturated normal hydrocarbon group having a carbon number of 11 to 21.

The third step: a step of preparing a suspension of a charged niosome by mixing the suspension of the niosome obtained in the first step with the cationic-surfactant aqueous solution obtained in the second step and allowing the cationic surfactant to modify a surface of the niosome with a positive charge of the hydrophilic part of the cationic surfactant.

[2] The First Step of the Preparing Method

Figure 1A:
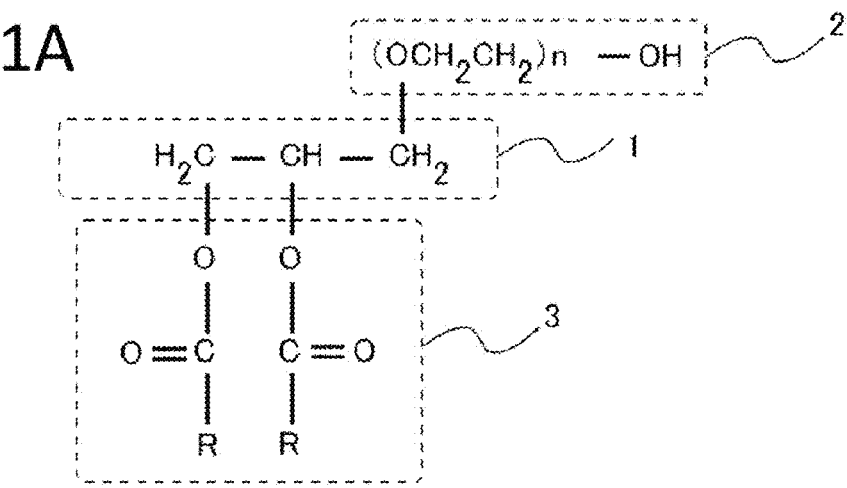
FIGS. 1A, 1B, 1C, 1D, and 1E are schematic chemical structural formulas.

FIG. 1A schematically shows the structure of a diacylglycerol PEG adduct equivalent to a main lipid used in the first step. A reference numeral 1 denotes the glycerol skeletal part schematically and a reference numeral 2 denotes the hydrophilic part schematically in which normal polyethylene glycol (PEG) is bonded to one piece of the three pieces of carbon. A reference numeral 3 denotes the hydrophobic part schematically in which a diacyl group consisting of two fatty acids is bonded individually to two pieces of the three pieces of carbon of the glycerol skeleton. A specific diacylglycerol PEG adduct will be below expressed as the " . . . acid glycerol PEG-n" on the basis of the kind of a fatty acid and the number n of PEG chains.

As the diacylglycerol PEG adduct, one or a plurality may be preferably chosen and used from a group which consists of glycerol PEG dioleate-12, glycerol PEG dimyristate-12, glycerol PEG dipalmitate-23, glycerol PEG distearate-12 and glycerol PEG distearate-23. The diacylglycerol PEG adducts have configurative requirements and mechanical requirements in the molecular structures for forming a niosome spontaneously only by mixing them with an aqueous solution. In other words, the diacylglycerol PEG adducts have suitable sizes, hardness, bending elastic moduli and the like for forming the niosome spontaneously in the aqueous solution.

The diacylglycerol PEG adduct used in the present invention has a melting point between a general preparation temperature range of 0° C. to 100° C. The diacylglycerol PEG adduct is mixed with a specified aqueous solution at a temperature where it will be in a liquid state, so that it can form a niosome spontaneously. In addition, as one of the conditions for forming a niosome spontaneously, the percentage of the lipid to the whole mixed liquid in the first step may preferably be approximately 2 mass % to 50 mass %, even though it is not necessarily strictly limited to this range. If the percentage of the lipid is raised beyond the range, then structures other than that of a niosome, such as a lamellar structure and an inverted hexagonal structure, may be easily formed.

With respect to the preparation temperature, for example, glycerol PEG dioleate-12 and glycerol PEG dimyristate-12 may be within a range of approximately 20° C. to 60° C., glycerol PEG dipalmitate-23 may be within a range of approximately 37° C. to 60° C., and glycerol PEG distearate-12 and glycerol PEG distearate-23 may be near approximately 60° C. It is confirmed that each of them is only mixed at the corresponding temperature with a specified aqueous solution to form a niosome spontaneously (refer to Patent Document 1).

The niosome spontaneously formed in the first step is extremely stable, and the formation of the niosome under the same conditions can be excellently reproduced. In addition, on a manufacturing scale, the niosome can be securely sterilized and the size, number and quality thereof between batches can also be kept uniform (refer to Patent Document 1).

The niosome contains diacylglycerol PEG adduct as a main constituent thereof, and further, may contain another lipid as a constituent thereof. Another such additional lipid needs to meet the conditions that the lipid is at least in a liquid state at a mixing temperature thereof. As this lipid, for example, a sterol such as cholesterol or an ester thereof may be used, and cholesterol is useful, for example, for stabilizing the niosome in the human body.

The specified aqueous solution in the first step is an aqueous solution which contains an objective substance, or the active ingredients or the like of medicaments, cosmetics and the like, dissolved therein, the objective substance being to be encapsulated in the niosome. The specified aqueous solution is encapsulated in a water phase at the center of the niosome and is also present around the niosome. In the first step, in the specified aqueous solution, the niosome are dispersed to obtain a suspension.

[3] The Second Step of the Preparing Method

Next, the cationic surfactant used in the second step is one or a plurality of cationic surfactants chosen from a group which consists of an aliphatic amine, an aliphatic or aliphatic-amide quaternary ammonium salt, an aliphatic amideamine and an acylamino acid derivative. The hydrophobic part of the cationic surfactant contains a saturated or unsaturated normal hydrocarbon group having a carbon number of 11 to 21. It may preferably contain only one such normal hydrocarbon group in the molecule.

Figure 1B:
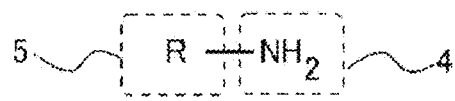

FIG. 1B shows a constitution example of a primary amine as an example of the aliphatic amine.

Figure 1C:
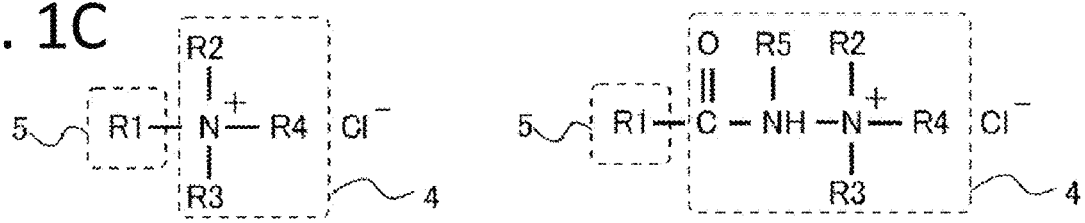

FIG. 1C shows a constitution example of the aliphatic or aliphatic-amide quaternary ammonium salt: the aliphatic quaternary ammonium salt is on the left and the aliphatic-amide quaternary ammonium salt is on the right.

Figure 1D:
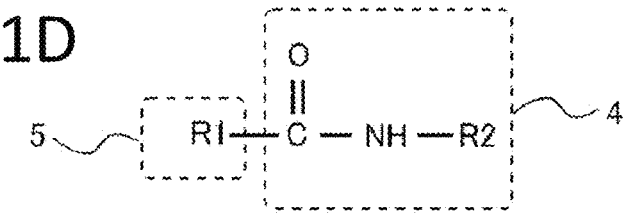

FIG. 1D shows a constitution example of a secondary amide as an example of the aliphatic amideamine.

Figure 1E:
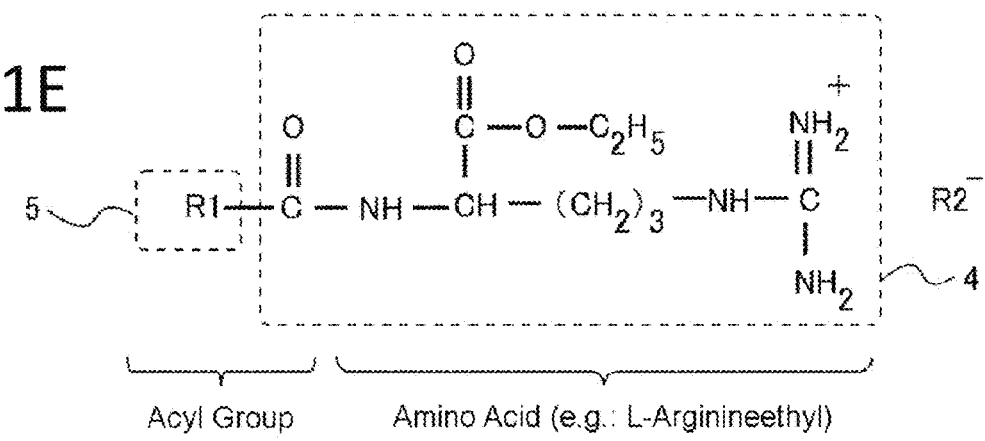

FIG. 1E shows a constitution example of the acylamino acid derivative. The acylamino acid derivative here means the cationic surfactant of an amino acid system containing an acyl group. The figure shows L-arginineethyl as an example of the amino acid part.

In FIGS. 1B-1E a reference numeral 4 schematically denotes the hydrophilic part which becomes an ion having a positive charge in the aqueous solution and a reference numeral 5 schematically denotes the hydrophobic part consisting of a saturated or unsaturated normal hydrocarbon group.

The aliphatic amine may preferably be a primary, secondary or tertiary amine. For example, it may preferably be one or a plurality chosen from a group which consists of tetradecylamine, palmitylamine, stearylamine, oleylamine, linoleylamine, behenylamine, N,N-dimethyldodecylamine and N,N-dimethyl-n-octadecylamine.

The aliphatic or aliphatic-amide quaternary ammonium salt may preferably be a quaternary ammonium salt. For example, the aliphatic quaternary ammonium salt may preferably be one or a plurality chosen from a group which consists of tetradecyltrimethyl ammonium chloride, cetyltrimethyl ammonium chloride, stearyltrimethyl ammonium chloride, behenyltrimethyl ammonium chloride and palmitamidopropyltrimethyl ammonium chloride.

The aliphatic amideamine may preferably be a primary, secondary or tertiary amideamine. For example, it may preferably be one or a plurality chosen from a group which consists of diethylaminoethylamide myristate, dimethylaminoethylamide myristate, dimethylaminopropylamide myristate, dimethylaminopropylamide myristate, diethylaminoethylamide palmitate, dimethylaminoethylamide palmitate, dimethylaminopropylamide palmitate, diethylaminopropylamide palmitate, diethylaminoethylamide stearate, dimethylaminoethylamide stearate, dimethylaminopropylamide stearate, diethylaminopropylamide stearate, diethylaminoethylamide behenate, dimethylaminoethylamide behenate, dimethylaminopropylamide behenate and diethylaminopropylamide behenate.

The acylamino acid derivative may preferably be a cocoylarginineethyl PCA. In the cocoylarginineethyl PCA, the R1-CO acyl group part in FIG. 1(b4) originates in a coconutoil fatty acid (mixture of a lauric acid, a myristic acid, a palmitic acid and the like) and R2⁻i0s a DL-PCA (dl-pyrrolidone calboxylic acid).

The acidic aqueous solution mixed with the cationic surfactant is, for example, a lactic-acid aqueous solution or a citric-acid aqueous solution. The acidic aqueous solution may preferably be equal to, or less than, pH4, even though it is not necessarily strictly limited to this value. The cationic surfactant is dissolved in the acidic aqueous solution, and thereby, the hydrophilic part thereof has a positive charge in the aqueous solution.

[4] The Third Step of the Preparing Method

In the third step, the suspension of the niosome obtained in the first step and the cationic-surfactant aqueous solution obtained in the second step are mixed together to prepare a suspension of a charged niosome. Specifically, for example, a post insertion method is utilized where the mixed liquid is stirred at a predetermined temperature for a predetermined period of time by a vortex or a machine.

Figure 2:
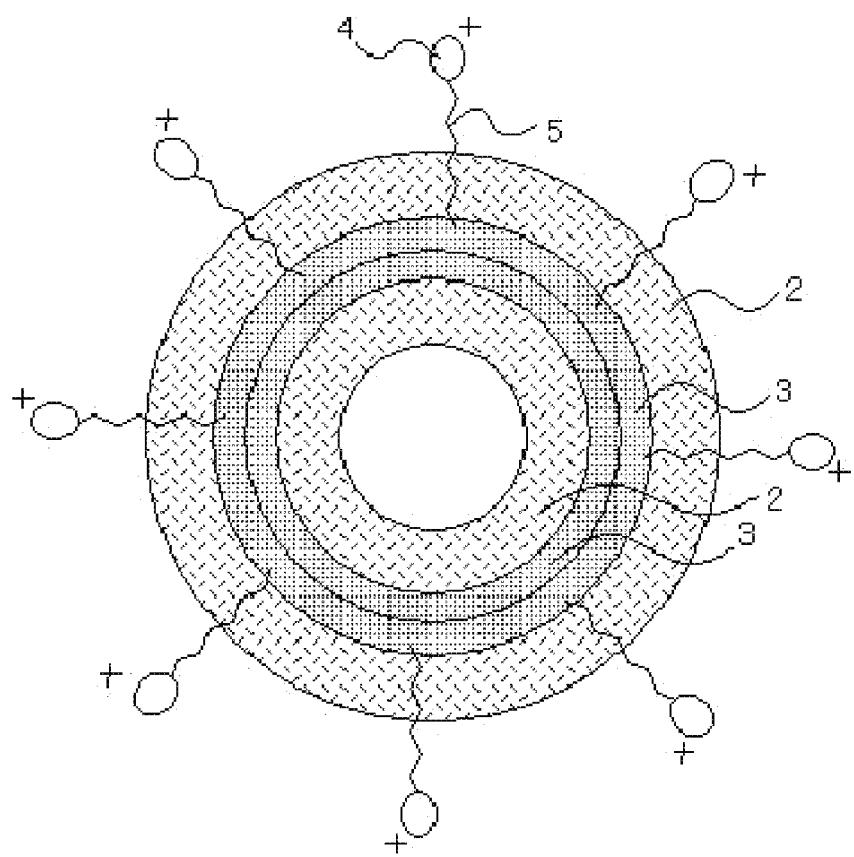
FIG. 2 is a sectional view of an image of a charged niosome obtained in the third step.

FIG. 2 is a sectional view of an image of the charged niosome obtained in the third step. As an example here, the niosome obtained in the first step has a double membrane. A PEG-chain hydrophilic part 2 is present on the surface thereof. The distal end of a hydrophobic part 5 of the cationic surfactant adheres or bonds to a hydrophobic part 3 inside of the shell of the niosome. The hydrocarbon chain of the hydrophobic part 5 protrudes and extends from the surface of the niosome, and a hydrophilic part 4 is present at the front end thereof. The hydrophilic part 4 is ionized and positively electrified in the aqueous solution.

In the third step, a suspension containing dispersed charged niosomes is obtained in the mixed aqueous solution obtained by mixing the aqueous solution in the first step and the aqueous solution in the second step. In the suspension, an objective substance dissolved in the aqueous solution is encapsulated in the water phase inside of the charged niosome.

In this way, the suspension of the charged niosome is prepared, and the suspension is used for obtaining a product which contains the charged niosome, such as medicaments and cosmetics. For example, in the third step, a lotion ingredient is mixed with the above to obtain a lotion preparation. In addition, a milky lotion, a gel or a cream prepared separately from the first to third steps is mixed therewith to obtain a milky lotion preparation, a gel preparation or a cream preparation.

WORKING EXAMPLES

Working examples of the above preparing method for the charged niosome, and results of tests for the surface charge, impregnation into the skin/storage in the skin and the like of the prepared charged niosome, will be below described.

(1) Measurements of the Surface Charge

<Samples>

Table 1 shows an outline and constituent percentages of the preparing method for a charged niosome (Working Example 1) and a conventional niosome (Comparative Example 1) which are used for measuring the zeta potential of the charged niosome. In Working Example 1, as the specified aqueous solution, deionized water is used instead because of the sample for measuring the zeta potential, but this will not affect the results of the working example.

Table 1 gives the numerical value of each constituent, and in Working Example 1, those values indicate the mass % if the charged-niosome suspension obtained in the third step is 100 while in Comparative Example 1, those values indicate the mass % if the charged-niosome suspension obtained in the first step is 100 (In the following similar tables alike, the product obtained in the final step is 100, and the constituent percentages thereto in each step will be indicated by the mass %).

TABLE 1

| | (1)niosome suspension | | (2)cationic-surfactant aqueous solution | | | (3)charged-niosome suspension | | |
|---|---|---|---|---|---|---|---|---|
| | | | | 50% lactic- | | | | |
| Mass % | lipid *1 | deionized water | cationic surfactant *2 | acid aqueous solution | deionized water | (1) | (2) | deionized water |
| Working Example 1 | 2 | 5 | 0.4 | 0.6 | 4 | 7 | 5 | 88 |
| | | | | | Mass % | lipid*1 2 | | deionized water |
| | | | | | Comparative Example 1 | | | 5 |

*1 GDM-12
*2 SDMAPA

<Preparing Method>

Working Example 1

The first step: at room temperature, adding deionized water having a 5 mass % to glycerol PEG dimyristate-12 having a 2 mass % (hereinafter, called the "GDM-12" for short) and mixing them (stirring them by a vortex or a machine, which is the same as in the first step of each of the other working examples), so that a niosome suspension is obtained.

The second step: dissolving dimethylaminopropylamide stearate having a 0.4 mass % (hereinafter, called the "SDMAPA" for short) completely in a 50% lactic-acid aqueous solution having a 0.6 mass % at a temperature of 70-80° C. and thereafter cooling it up to a room temperature of 30° C. or below, so that an SDMAPA aqueous solution is obtained.

The third step: adding the SDMAPA aqueous solution at the second step to the niosome suspension at the first step, mixing them (stirring them by a vortex or a machine, which is the same as in the third step of each of the other working examples), thereafter adding deionized water having an 88 mass % to it and mixing them.

Comparative Example 1

At room temperature, deionized water having a 98 mass % is added to GDM-12 having a 2 mass %, and they are mixed and stirred, so that a niosome suspension is obtained.

<Measurement Results of Zeta Potential>

Figure 3A:
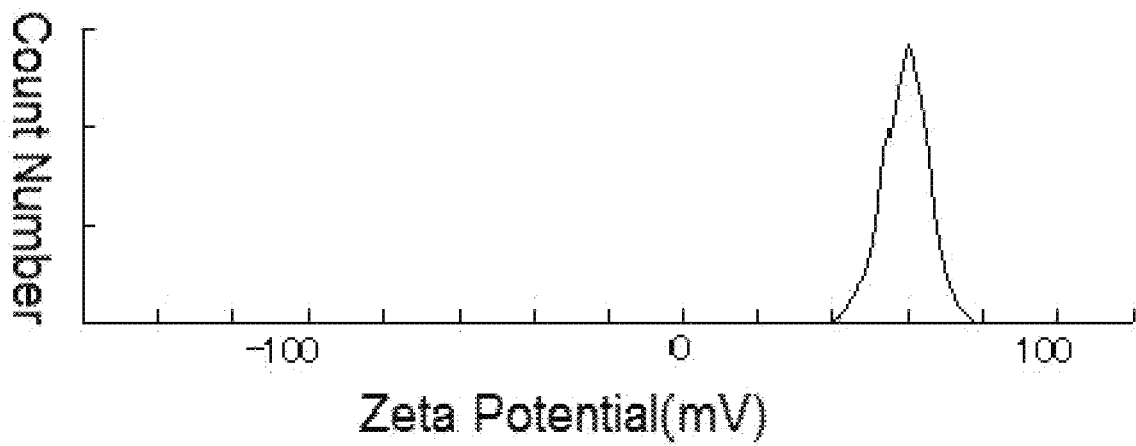
FIG. 3A-3B is a graphical representation showing measurement results of the zeta potential in Working Example 1 and Comparative Example 1 respectively.
Figure 3B:
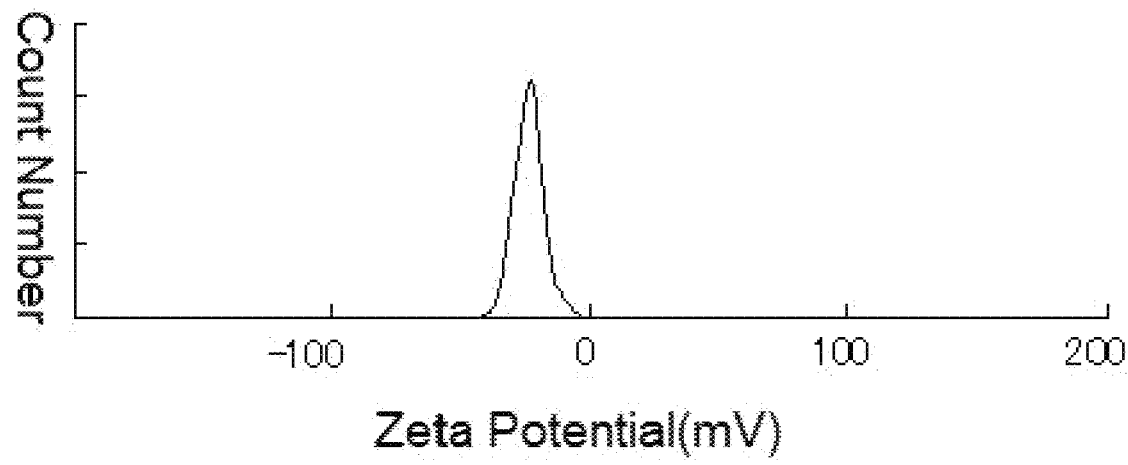

FIG. 3A-3B s a graphical representation showing measurement results of the zeta potential in Working Example 1 and Comparative Example 1 respectively. The horizontal axis indicates the potential. In Working Example 1, the peak appears within a range of 60 mV to 80 mV, which means being positively electrified. In Comparative Example 1, the peak appears within a range of −10 mV to 20 mV.

(2) Photomicrographs by the Electron Microscope

FIGS. 4A-4B are photomicrographs taken through a transmission electron microscope (TEM) in Working Example 1 and Comparative Example 1 respectively. In Working Example 1 of FIG. 4A a dyeing agent for negative dyeing comes into contact with a charge on the surface, and a surface charge is observed. In Comparative Example 1 of FIG. 4B a multiple layer in the form of a concentric circle is observed, and no surface structure is seen. The charged niosome of Working Example 1 is considered to be the structure of the niosome of Comparative Example 1 having an outermost-layer surface electrified with a positive charge.

(3) Percutaneous Absorption Tests—Trial 1

<Samples>

Table 2 shows an outline and constituent percentages of the preparing method for the charged niosome (Working Example 2), a conventional niosome (Comparative Example 2a) and the aqueous solution (Comparative Example 2b) which are used in percutaneous absorption tests carried out by encapsulating Calcein Na equivalent to a fluorescent labeling substance.

having a 0.6 mass % at a temperature of 70-80° C. and thereafter cooling it up to a room temperature of 30° C. or below, so that an SDMAPA aqueous solution is obtained.

The third step: adding the SDMAPA aqueous solution at the second step to the niosome suspension at the first step, stirring them softly so that a yellowish-brown viscous solution is obtained, thereafter adding deionized water having an 88 mass % to it and stirring them softly, so that a yellowish-brown charged-niosome suspension is obtained.

Comparative Example 2a

At room temperature, a Calcein-Na containing aqueous solution having a 5 mass % (Calcein Na having a 0.5 mass % and deionized water having a 4.5 mass %) and deionized water having a 93 mass % are added to GDM-12 having a 2 mass %, and they are softly stirred, so that a niosome suspension is obtained.

Comparative Example 2b

The first step: mixing a Calcein-Na containing aqueous solution having a 5 mass % (Calcein Na having a 0.5 mass % and deionized water having a 4.5 mass %) and deionized water having a 95 mass %, so that a Calcein-Na containing aqueous solution is obtained.

<Results>

Figure 5:
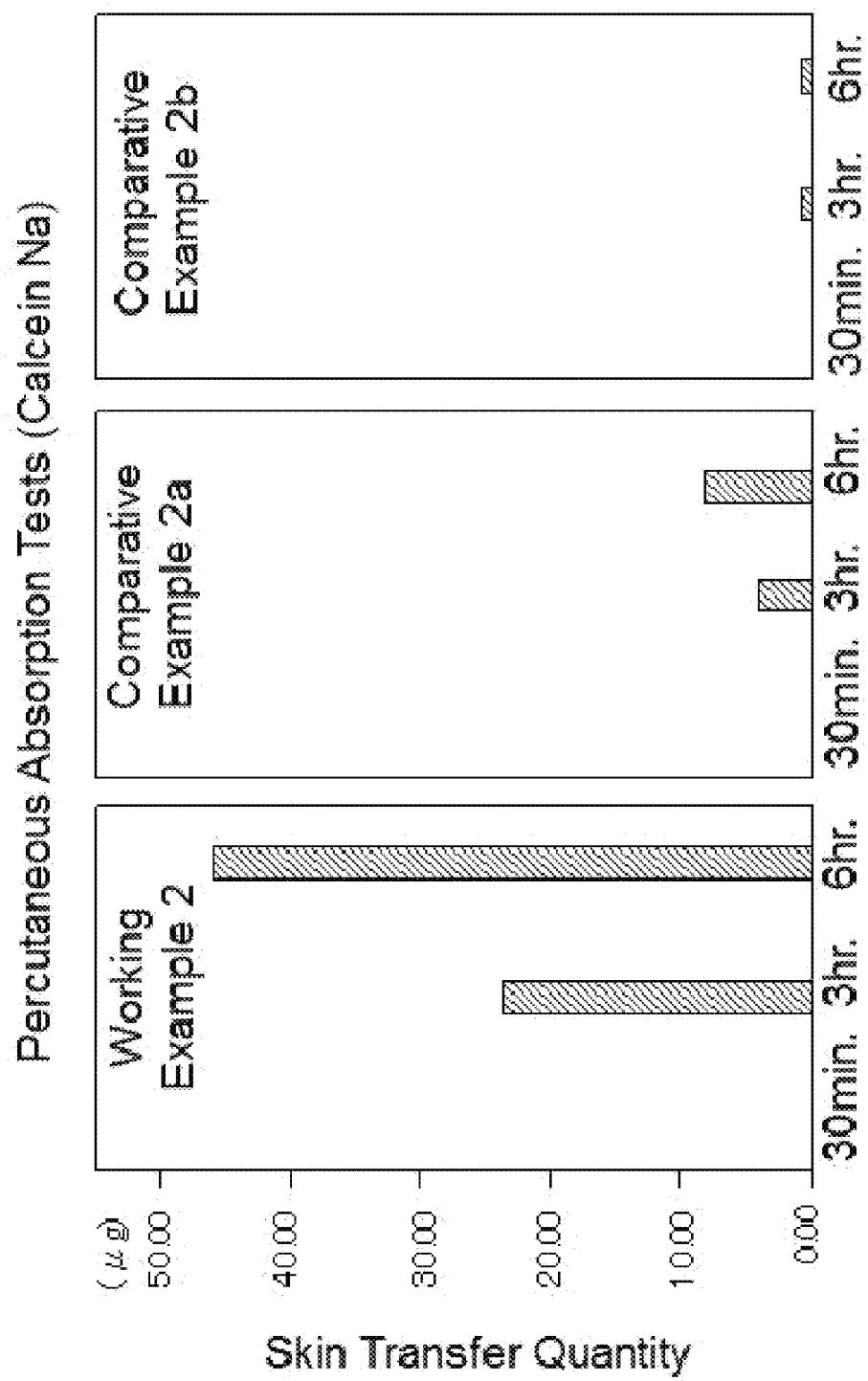
FIG. 5 is a graphical representation showing test results for the percutaneous absorption in Working Example 2 and Comparative Examples 2a and 2b respectively.

FIG. 5 is a graphical representation showing test results for the percutaneous absorption in Working Example 2 and Comparative Examples 2a and 2b respectively. The skin transfer quantity indicates the sum of the quantity of Calcein Na remaining in the skin (horny layer) (intra-skin quantity) and the quantity of Calcein Na which has permeated the skin (skin permeation quantity) at each point of time when 30

TABLE 2

| Mass % | (1) niosome suspension | | (2) cationic-surfactant aqueous solution | | | (3) charged-niosome suspension | | |
|---|---|---|---|---|---|---|---|---|
| | lipid *1 | calcein-Na containing aqueous solution *2 | cationic surfactant *3 | 50% lactic-acid aqueous solution | deionized water | (1) | (2) | deionized water |
| Working Example 2 | 2 | 5 | 0.4 | 0.6 | 4 | 7 | 5 | 88 |

| Mass % | lipid *1 | calcein-Na containing aqueous solution | deionized water |
|---|---|---|---|
| Comparative Example 2a | 2 | 5 | 93 |
| Comparative Example 2b | | 9 | 95 |

*1 GDM-12
*2 calcein Na (0.5 mass %) + deionized water (4.5 mass %)
*3 SDMAPA

<Preparing Method>

Working Example 2

The first step: at room temperature, adding a Calcein-Na containing aqueous solution having a 5 mass % (Calcein Na having a 0.5 mass % and deionized water having a 4.5 mass %) to the GDM-12 having a 2 mass % and mixing them, so that a yellowish-brown viscous niosome suspension is obtained.

The second step: dissolving the SDMAPA having a 0.4 mass % completely in a 50% lactic-acid aqueous solution minutes, 3 hours and 6 hours have elapsed after applied to the skin surface. In Working Example 2, the impregnation into the skin is quite excellent, as compared with Comparative Examples 2a and 2b.

(4) Percutaneous Absorption Tests—Trial 2

<Samples>

Tables 3 and 4 each show an outline and constituent percentages of the preparing method for the charged niosome (Working Examples 3 and 4) and a conventional niosome (Comparative Examples 3a and 4a) which are used in percutaneous absorption tests carried out by encapsulating Calcein Na equivalent to a fluorescent labeling substance.

TABLE 3

| Mass % | (1)niosome suspension calcein-Na containing aqueous solution lipid *1 | (1)niosome suspension calcein-Na containing aqueous solution *2 | (2)cationic-surfactant aqueous solution cationic surfactant *3 | (2)cationic-surfactant aqueous solution 50% lactic-acid aqueous solution | (2)cationic-surfactant aqueous solution deionized water | (3)charged-niosome suspension (1) | (3)charged-niosome suspension (2) | (3)charged-niosome suspension deionized water | (3)charged-niosome suspension 1,3-butylene glycol | (3)charged-niosome suspension 1,3-propanediol |
|---|---|---|---|---|---|---|---|---|---|---|
| Working Example 3 | 2 | 5 | 0.4 | 0.6 | 4 | 7 | 5 | 66 | 7 | 15 |

| Mass % | | lipid *1 | calcein-Na containing aqueous solution *2 | deionized water | 1,3-butylene glycol | 1,3-propanediol |
|---|---|---|---|---|---|---|
| Comparative Example 3a | | 2 | 5 | 71 | 7 | 15 |

*1 GDM-12
*2 calcein Na (0.1 mass %) + deionized water (4.9 mass %)
*3 SDMAPA

TABLE 4

| Mass % | (1)niosome suspension lipid *1 | (1)niosome suspension calcein-Na containing aqueous solution *2 | (2)cationic-surfactant aqueous solution cationic surfactant *3 | (2)cationic-surfactant aqueous solution 50% lactic-acid aqueous solution | (2)cationic-surfactant aqueous solution deionized water | (3)charged-niosome suspension (1) | (3)charged-niosome suspension (2) | (3)charged-niosome suspension deionized water |
|---|---|---|---|---|---|---|---|---|
| Working Example 4 | 2.27 | 5 | 0.4 | 0.6 | 4 | 7.27 | 5 | 87.73 |

| Mass % | lipid *1 | calcein-Na containing aqueous solution | deionized water |
|---|---|---|---|
| Comparative Example 4a | 2.27 | 5 | 92.73 |

*1 GDM-12
*2 calcein Na (0.1 mass %) + deionized water (4.9 mass %)
*3 SDMAPA

<Preparing Method>

Working Example 3

The first step: at room temperature, adding a Calcein-Na containing aqueous solution having a 5 mass % (Calcein Na having a 0.1 mass % and deionized water having a 4.9 mass %) to the GDM-12 having a 2 mass % and mixing them, so that a yellowish-brown viscous niosome suspension is obtained.

The second step: dissolving the SDMAPA having a 0.4 mass % completely in a 50% lactic-acid aqueous solution having a 0.6 mass % at a temperature of 70-80° C. and thereafter cooling it up to a room temperature of 30° C. or below, so that an SDMAPA aqueous solution is obtained.

The third step: adding the SDMAPA aqueous solution at the second step to the niosome suspension at the first step, stirring them softly so that a yellowish-brown viscous solution is obtained, thereafter adding deionized water having a 66 mass %, 1,3-butylene glycol having a 7 mass % and 1,3-propanediol having a 15 mass % to it and stirring them softly, so that a yellowish-brown charged-niosome suspension is obtained.

Comparative Example 3a

At room temperature, a Calcein-Na containing aqueous solution having a 5 mass % (Calcein Na having a 0.1 mass % and deionized water having a 4.9 mass %) and deionized water having a 71 mass %, 1,3-butylene glycol having a 7 mass % and 1,3-propanediol having a 15 mass % are added to GDM-12 having a 2 mass %, and they are softly stirring, so that a niosome suspension is obtained.

Working Example 4

The first step: at room temperature, adding a Calcein-Na containing aqueous solution having a 5 mass % (Calcein Na having a 0.1 mass % and deionized water having a 4.9 mass %) to the GDM-12 having a 2.27 mass % and mixing them, so that a yellowish-brown viscous niosome suspension is obtained.

The second step: dissolving the SDMAPA having a 0.4 mass completely in a 50% lactic-acid aqueous solution having a 0.6 mass % at a temperature of 70-80° C. and thereafter cooling it up to a room temperature of 30° C. or below, so that an SDMAPA aqueous solution is obtained.

The third step: adding the SDMAPA aqueous solution at the second step to the niosome suspension at the first step, stirring them softly so that a yellowish-brown viscous solution is obtained, thereafter adding deionized water having an 87.73 mass % to it and stirring them softly, so that a yellowish-brown charged-niosome suspension is obtained.

Comparative Example 4a

At room temperature, a Calcein-Na containing aqueous solution having a 5 mass % (Calcein Na having a 0.1 mass % and deionized water having a 4.9 mass %) and deionized water having a 92.73 mass % are added to GDM-12 having a 2.27 mass %, and they are softly stirring, so that a niosome suspension is obtained.

<Results>

Figure 6:
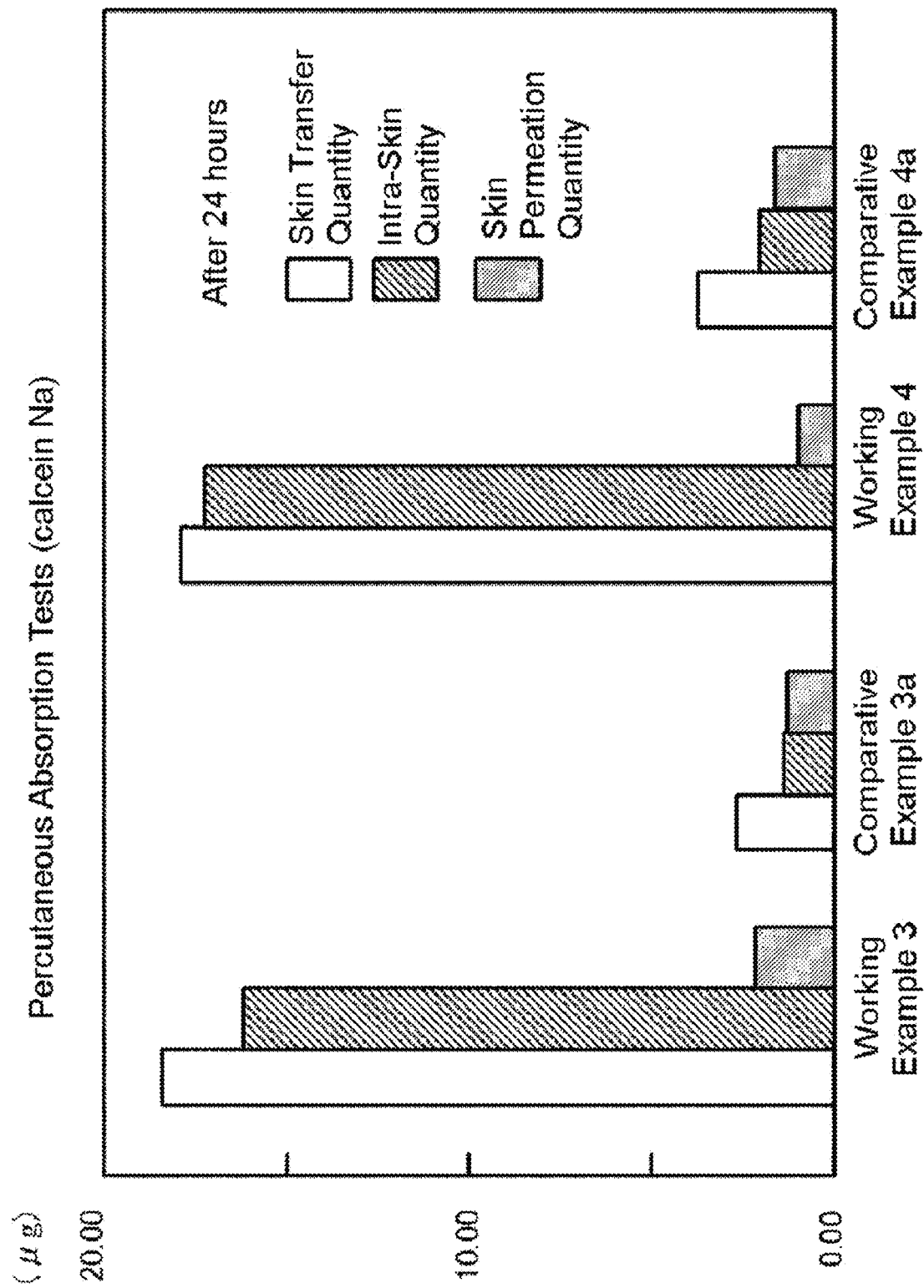
FIG. 6 is a graphical representation showing test results for the percutaneous absorption in Working Examples 3 and 4 and Comparative Examples 3a and 4a respectively.

FIG. 6 is a graphical representation showing test results for the percutaneous absorption in Working Examples 3 and 4 and Comparative Examples 3a and 4a respectively. The graph indicates the transfer quantity of Calcein Na from the skin surface into the skin (skin transfer quantity), the quantity of Calcein Na remaining in the skin (horny layer) (intra-skin quantity) and the quantity of Calcein Na which has permeated the skin (skin permeation quantity) at the point of time when 24 hours have elapsed after applied to the skin surface. In Working Examples 3 and 4, the impregnation into the skin and the storage in the skin are quite excellent, as compared with Comparative Examples 3a and 4a. The skin storage percentages are 88% and 96% in Working Examples 3 and 4 respectively, while the skin storage percentages are between approximately 51-56% in Comparative Examples 3a and 4a. The skin storage percentages are calculated in the expression of [intra-skin quantity/skin transfer quantity]×100%.

(5) Percutaneous Absorption Tests—Trial 3
<Samples>

Table 5 shows an outline and constituent percentages of the preparing method for the charged niosome (Working Example 5), a conventional niosome (Comparative Example 5a) and 3-O-ethylascorbic acid aqueous solution (Comparative Example 5b) which are used in percutaneous absorption tests 3 carried out by encapsulating 3-O-ethylascorbic acid.

TABLE 5

| | (1) niosome suspension | | | (2) cationic-surfactant aqueous solution | | |
|---|---|---|---|---|---|---|
| Mass % | lipid *1 | 3-O-ethylascorbic acid aqueous solution | cationic surfactant | 50% lactic-acid aqueous solution | deionized water | |
| Working Example 5 | 2 | 10 | 0.4 | 0.6 | 4 | |

| | (3) charged-niosome suspension | | | | | |
|---|---|---|---|---|---|---|
| Mass % | (1) | (2) | deionized water | glycerol | 1,3-butylene glycol | 1,2-pentanediol |
| Working Example 5 | 12 | 5 | 73 | 5 | 3 | 2 |

| Mass % | lipid *1 | 3-O-ethylascorbic acid aqueous solution *2 | deionized water | glycerol | 1,3-butylene glycol | 1,2-pentanediol |
|---|---|---|---|---|---|---|
| Comparative Example 5a | 2 | 10 | 78 | 5 | 3 | 2 |
| Comparative Example 5b | | 10 | 80 | 5 | 3 | 2 |

*1 GDM-12
*2 3-O-ethylascorbic acid (5 mass %) + deionized water (5 mass %)
*3 SDMAPA <Preparing Method>

Working Example 5

The first step: at room temperature, adding a 3-O-ethylascorbic-acid containing aqueous solution having a 10 mass % (3-O-ethylascorbic acid having a 5 mass % and deionized water having a 5 mass %) to the GDM-12 having a 2 mass % and mixing them, so that a niosome suspension is obtained.

The second step: dissolving the SDMAPA having a 0.4 mass % completely in a 50% lactic-acid aqueous solution having a 0.6 mass % at a temperature of 70-80° C. and thereafter cooling it up to a room temperature of 30° C. or below, so that an SDMAPA aqueous solution is obtained.

The third step: adding the SDMAPA aqueous solution at the second step to the niosome suspension at the first step, stirring them softly so that a solution is obtained, thereafter adding deionized water having a 73 mass %, glycerol having a 5 mass %, 1,3-butylene glycol having a 3 mass % and 1,2-pentanediol having a 2 mass % to it and stirring them softly, so that a charged-niosome suspension is obtained.

Comparative Example 5a

At room temperature, a 3-O-ethylascorbic-acid containing aqueous solution having a 10 mass % (3-O-ethylascorbic acid having a 5 mass % and deionized water having a 5 mass %), deionized water having a 78 mass %, glycerol having a 5 mass %, 1,3-butylene glycol having a 3 mass % and 1,2-pentanediol having a 2 mass % are added to GDM-12 having a 2 mass %, and they are softly stirring, so that a niosome suspension is obtained.

Comparative Example 5b

At room temperature, a 3-O-ethylascorbic-acid containing aqueous solution having a 10 mass % (3-O-ethylascorbic acid having a 5 mass % and deionized water having a 5 mass %), deionized water having an 80 mass %, glycerol having a 5 mass %, 1,3-butylene glycol having a 3 mass % and 1,2-pentanediol having a 2 mass % are mixed together, so that a 3-O-ethylascorbic-acid containing aqueous solution is obtained.

<Results>

Figure 7:
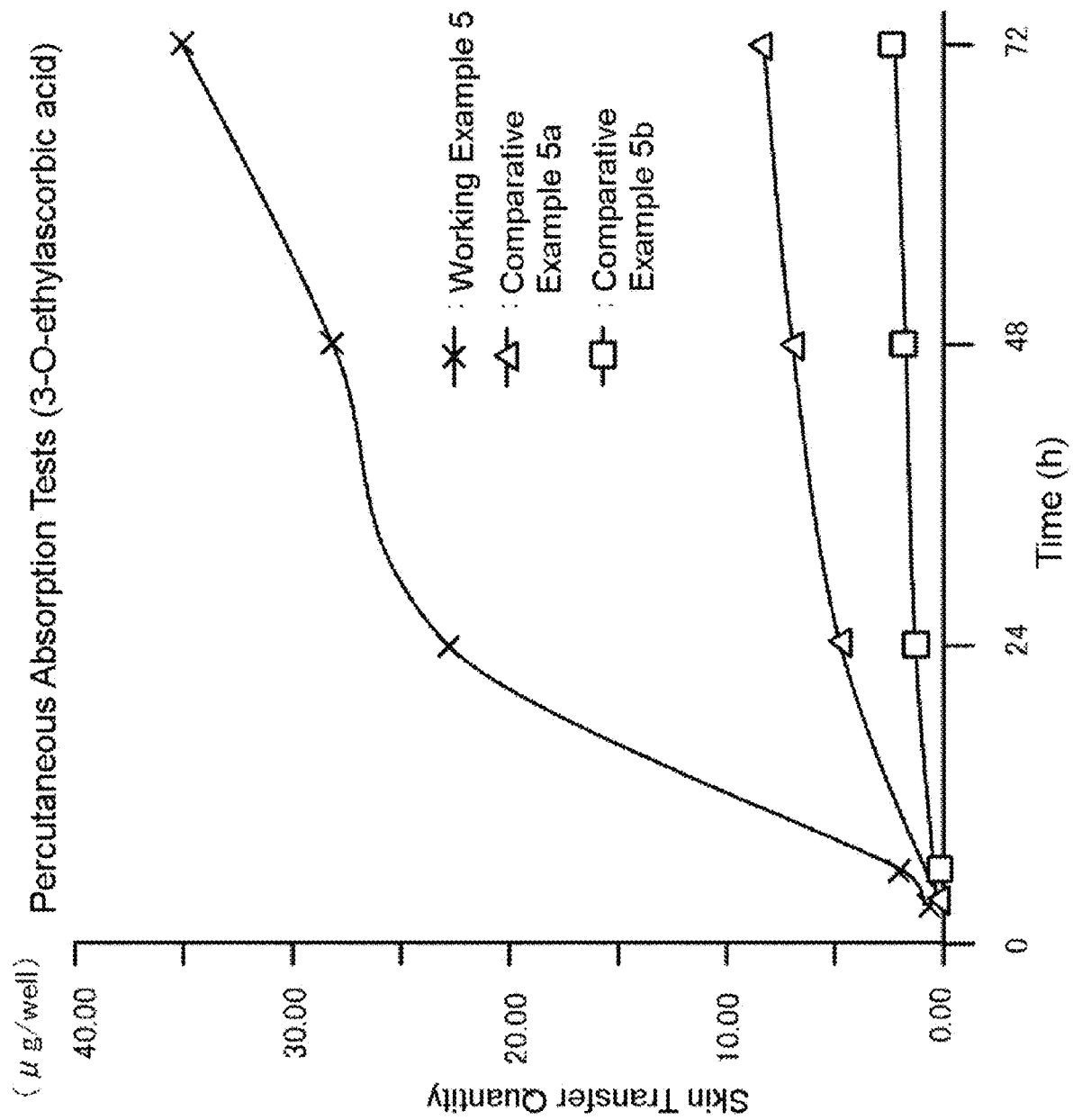
FIG. 7 is a graphical representation showing test results for the percutaneous absorption in Working Example 5 and Comparative Examples 5a and 5b respectively.

FIG. 7 is a graphical representation showing test results for the percutaneous absorption in Working Example 5 and Comparative Examples 5a and 5b respectively. The graph indicates changes in the skin permeation quantity as time goes by. In Working Example 5, as can be seen, the impregnation into the skin is quite excellent, as compared with the comparative examples. In Working Example 5, the charged niosome is excellently stored in the skin, and thereby, the skin permeation quantity keeps increasing over a long period of time.

(6) Percutaneous Absorption Tests—Trial 4

<Samples>

Tables 6 to 9 show an outline and constituent percentages of the preparing method for a lotion preparation (Working Example 6), a milky lotion preparation (Working Example 7), a gel preparation (Working Example 8) and a cream preparation (Working Example 9) of the charged niosome, and arbutin containing PBS (−) (Comparative Example 6a) and PBS (−) (Comparative Example 6b), which are used in percutaneous absorption tests 4 carried out by encapsulating arbutin.

TABLE 6

| | (1)niosome suspension | | (2)cationic-surfactant aqueous solution | | |
| --- | --- | --- | --- | --- | --- |
| Mass % | lipid *1 | arbutin aqueous solution | cationic surfactant | 50% lactic-acid aqueous solution | deionized water |
| Working Example 6 | 2 | 6 | 0.4 | 0.6 | 4 |

| | (3)charged-niosome suspension (lotion preparation) | | | | |
| --- | --- | --- | --- | --- | --- |
| Mass % | (1) | (2) | deionized water | glycerol | diglycerol | 1,3-butylene glycol |
| Working Example 6 | 8 | 5 | 76 | 6 | 1 | 4 |

| Mass % | arbutin | PBS (−) |
| --- | --- | --- |
| Comparative Example 6a | 1 | 99 |
| Comparative Example 6b | | 100 |

*1 GDM-12
*2 arbutin (1 mass %) + deionized water (5 mass %)
*3 SDMAPA

TABLE 7

| | (1)niosome suspension | | (2)cationic-surfactant aqueous solution | | | (3)charged-niosome suspension | | |
| --- | --- | --- | --- | --- | --- | --- | --- | --- |
| Mass % | lipid *1 | arbutin aqueous solution *2 | cationic surfactant *3 | 50% lactic-acid aqueous solution | deionized water | (1) | (2) | deionized water |
| Working Example 7 | 2 | 6 | 0.4 | 0.6 | 4 | 8 | 5 | 7 |

| | (4)milky lotion | | | | | | | (5)milky lotion preparation |
| --- | --- | --- | --- | --- | --- | --- | --- | --- |
| Mass % | deionized water | glycerol | diglycerol | 1,3-butylene glycol | squalane | cetyl alcohol | TINOVIS ® CD | (3) | (4) |
| Working Example 7 | 61.5 | 6 | 1 | 4 | 6 | 1 | 0.5 | 20 | 80 |

*1 GDM-12
*2 arbutin (1 mass %) + deionized water (5 mass %)
*3 SDMAPA

TABLE 8

| Mass % | (1) niosome suspension | | (2) cationic-surfactant aqueous solution | | | (3) charged-niosome suspension | | |
|---|---|---|---|---|---|---|---|---|
| | lipid *1 | arbutin aqueous solution *2 | cationic surfactant *3 | 50% lactic-acid aqueous solution | deionized water | (1) | (2) | deionized water |
| Working Example 8 | 2 | 6 | 0.4 | 0.6 | 4 | 8 | 5 | 7 |

| Mass % | (4) gel | | | | | | (5) gel preparation | |
|---|---|---|---|---|---|---|---|---|
| | deionized water | glycerol | diglycerol | 1,3-butylene glycol | cetyl alcohol | TINOVIS® CD | (3) | (4) |
| Working Example 8 | 66 | 6 | 1 | 4 | 2 | 1 | 20 | 80 |

*1 GDM-12
*2 arbutin (1 mass %) + deionized water (5 mass %)
*3 SDMAPA

TABLE 9

| Mass % | (1) niosome suspension | | (2) cationic-surfactant aqueous solution | | | (3) charged-niosome suspension | | |
|---|---|---|---|---|---|---|---|---|
| | lipid *1 | arbutin aqueous solution *2 | cationic surfactant *3 | 50% lactic-acid aqueous solution | deionized water | (1) | (2) | deionized water |
| Working Example 9 | 2 | 6 | 0.4 | 0.6 | 4 | 8 | 5 | 7 |

| Mass % | (4) cream | | | | | | | |
|---|---|---|---|---|---|---|---|---|
| | deionized water | glycerol | diglycerol | 1,3-butylene glycol | polyethylene glycol monostearate | glyceryl stearate | cetyl alcohol | squalane |
| Working Example 9 | 47.5 | 6 | 1 | 4 | 1.4 | 1.6 | 2.5 | 1.6 |

| | (5) cream preparation | |
|---|---|---|
| Mass % | (3) | (4) |
| Working Example 9 | 20 | 80 |

*1 GDM-12
*2 arbutin (1 mass %) + deionized water (5 mass %)
*3 SDMAPA

<Preparing Method>

Working Example 6

The first step: at room temperature, adding an arbutin containing aqueous solution having a 6 mass % (arbutin having a 1 mass % and deionized water having a 5 mass %) to the GDM-12 having a 2 mass % and mixing them, so that a white viscous niosome suspension is obtained.

The second step: dissolving the SDMAPA having a 0.4 mass % completely in a 50% lactic-acid aqueous solution having a 0.6 mass % at a temperature of 70-80° C. and thereafter cooling it up to a room temperature of 30° C. or below, so that an SDMAPA aqueous solution is obtained.

The third step: adding the SDMAPA aqueous solution at the second step to the niosome suspension at the first step, stirring them softly so that a viscous solution is obtained, thereafter adding deionized water having a 76 mass %, glycerol having a 6 mass %, diglycerol having a 6 mass % and 1,3-butylene glycol having a 4 mass % to it and stirring them softly, so that a lotion preparation formed of a charged-niosome suspension is obtained.

Comparative Example 6a

At room temperature, arbutin having a 1 mass % and PBS (−) having a 99 mass % are mixed together, so that an arbutin PBS (−) aqueous solution is obtained.

Comparative Example 6b

PBS (−) itself is directly used.

Working Example 7

The first step: at room temperature, adding an arbutin containing aqueous solution having a 6 mass % (arbutin having a 1 mass % and deionized water having a 5 mass %) to the GDM-12 having a 2 mass % and mixing them, so that a white viscous niosome suspension is obtained.

The second step: dissolving the SDMAPA having a 0.4 mass % completely in a 50% lactic-acid aqueous solution having a 0.6 mass % at a temperature of 70-80° C. and thereafter cooling it up to a room temperature of 30° C. or below, so that an SDMAPA aqueous solution is obtained.

The third step: adding the SDMAPA aqueous solution at the second step to the niosome suspension at the first step, stirring them softly so that a viscous solution is obtained, thereafter adding deionized water having a 76 mass % to it and stirring them softly, so that a charged-niosome suspension is obtained.

The fourth step: at a temperature of 80° C., mixing deionized water having a 61.5 mass %, glycerol having a 6 mass %, diglycerol having a 6 mass %, diglycerol having a 1 mass %, 1,3-butylene glycol having a 4 mass %, squalane having a 6 mass %, cetyl alcohol having a 1 mass % and Tinovis (registered trademark) CD (by BASF Corporation) having a 0.5 mass %, emulsifying it and thereafter cooling it up to room temperature, so that a milky lotion is obtained.

The fifth step: adding the charged-niosome suspension obtained at the third step to the milky lotion obtained at the fourth step, so that a milky lotion preparation is obtained.

Working Example 8

The first step: at room temperature, adding an arbutin containing aqueous solution having a 6 mass % (arbutin having a 1 mass % and deionized water having a 5 mass %) to the GDM-12 having a 2 mass % and mixing them, so that a white viscous niosome suspension is obtained.

The second step: dissolving the SDMAPA having a 0.4 mass % completely in a 50% lactic-acid aqueous solution having a 0.6 mass % at a temperature of 70-80° C. and thereafter cooling it up to a room temperature of 30° C. or below, so that an SDMAPA aqueous solution is obtained.

The third step: adding the SDMAPA aqueous solution at the second step to the niosome suspension at the first step, stirring them softly so that a viscous solution is obtained, thereafter adding deionized water having a 7 mass % to it and stirring them softly, so that a viscous charged-niosome suspension is obtained.

The fourth step: at a temperature of 80° C., mixing deionized water having a 66 mass %, glycerol having a 6 mass %, diglycerol having a 6 mass %, diglycerol having a 1 mass %, 1,3-butylene glycol having a 4 mass %, cetyl alcohol having a 2 mass % and Tinovis (registered trademark) CD (by BASF Corporation) having a 1 mass %, emulsifying it and thereafter cooling it up to room temperature, so that a viscous gel is obtained.

The fifth step: adding the charged-niosome suspension obtained at the third step to the gel obtained at the fourth step, so that a gel preparation is obtained.

Working Example 9

The first step: at room temperature, adding an arbutin containing aqueous solution having a 6 mass % (arbutin having a 1 mass % and deionized water having a 5 mass %) to the GDM-12 having a 2 mass % and mixing them, so that a white viscous niosome suspension is obtained.

The second step: dissolving the SDMAPA having a 0.4 mass % completely in a 50% lactic-acid aqueous solution having a 0.6 mass % at a temperature of 70-80° C. and thereafter cooling it up to a room temperature of 30° C. or below, so that an SDMAPA aqueous solution is obtained.

The third step: adding the SDMAPA aqueous solution at the second step to the niosome suspension at the first step, stirring them softly so that a viscous solution is obtained, thereafter adding deionized water having a 7 mass % to it and stirring them softly, so that a viscous charged-niosome suspension is obtained.

The fourth step: at a temperature of 80° C., mixing deionized water having a 47.5 mass %, glycerol having a 6 mass %, diglycerol having a 6 mass %, diglycerol having a 1 mass %, 1,3-butylene glycol having a 4 mass %, polyethylene glycol monostearate having a 1.4 mass %, glyceryl stearate having a 1.6 mass %, cetyl alcohol having a 2.5 mass % and squalane having a 16 mass %, emulsifying it and thereafter cooling it up to room temperature, so that a white cream is obtained.

The fifth step: adding the charged-niosome suspension obtained at the third step to the cream obtained at the fourth step, so that a cream preparation is obtained.

<Results>

Figure 8:
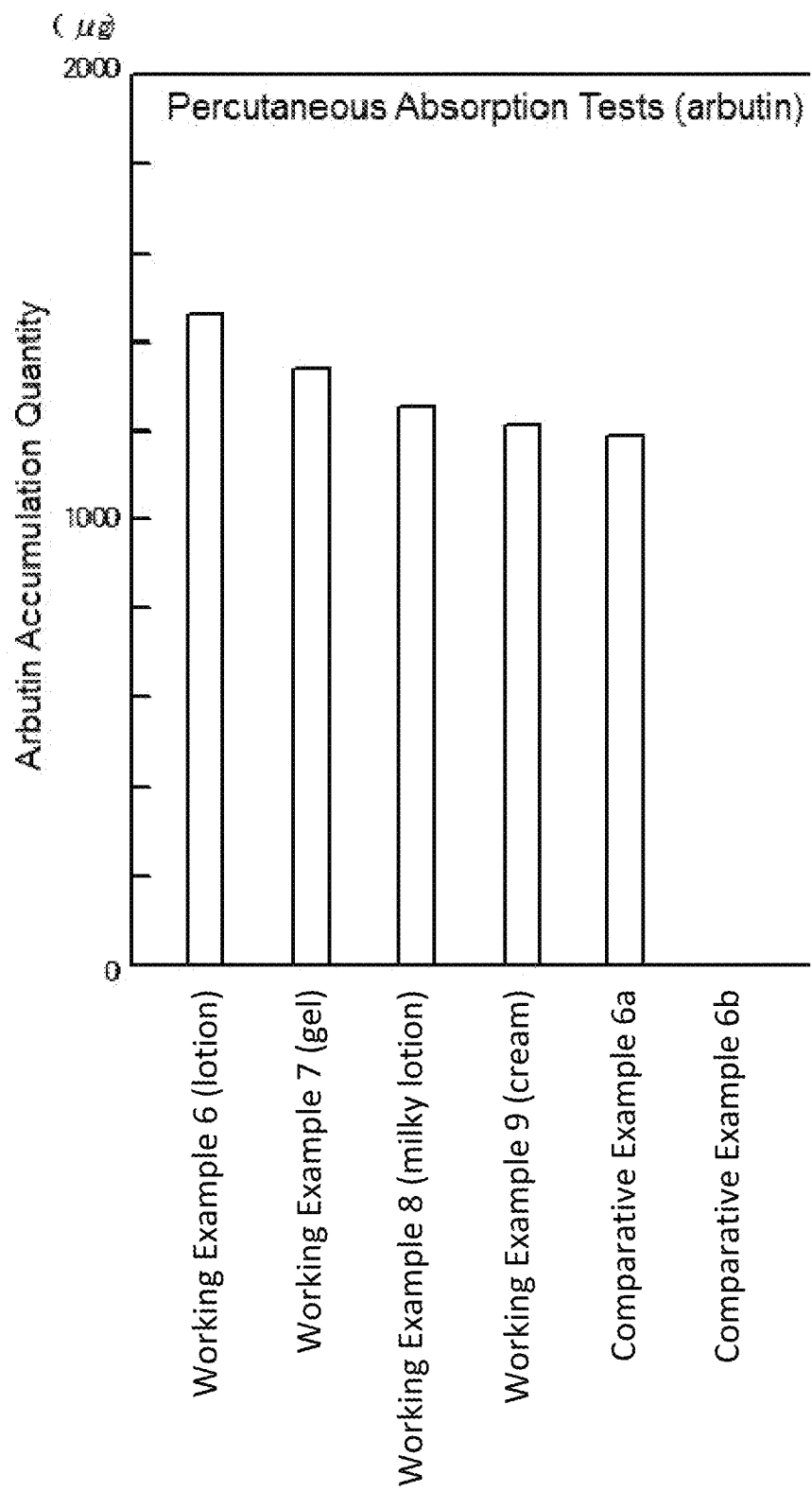
FIG. 8 is a graphical representation showing test results for the percutaneous absorption in Working Examples 6, 7, 8 and 9 and Comparative Examples 6a and 6b respectively.

FIG. 8 is a graphical representation showing test results for the percutaneous absorption in Working Examples 6, 7, 8 and 9 and Comparative Examples 6a and 6b respectively. The graph indicates the accumulation quantity in the skin. In the working examples, as can be seen, the impregnation into the skin and the storage in the skin are quite excellent, as compared with the comparative examples.

(7) Percutaneous Absorption Tests—Trial 5 and Skin-Whitening Effect Tests

<Samples>

Table 10 shows an outline and constituent percentages of the preparing method for an emulsifying preparation of the charged niosome (Working Example 10), an emulsifier of a niosome (Comparative Example 10a), an arbutin containing aqueous solution without a niosome (Comparative Example 10b), arbutin containing PBS (−) (Comparative Example 10c) and PBS (−) (Comparative Example 10d) which are used in percutaneous absorption tests 5 and skin-whitening effect tests carried out by encapsulating arbutin.

TABLE 10

| Mass % | (1) niosome suspension | | (2) cationic-surfactant aqueous solution | | | (3) charged-niosome suspension | | |
|---|---|---|---|---|---|---|---|---|
| | lipid *1 | arbutin aqueous solution *2 | cationic surfactant *3 | 50% lactic-acid aqueous solution | deionized water | (1) | (2) | deionized water |
| Working Example 10 | 2 | 6 | 0.4 | 0.6 | 4 | 8 | 5 | 7 |

| Mass % | (4) milky lotion | | | | | | | | | |
|---|---|---|---|---|---|---|---|---|---|---|
| | water | glycerol | diglycerol | 1,3-butylene glycol | 1,2-pentanediol | Mannan | polyethylene glycol monostearate | glyceryl stearate | squalane | cetyl alcohol |
| Working Example 10 | 58.85 | 6 | 1 | 4 | 1 | 0.3 | 1.4 | 1.6 | 6 | 1.5 |

| | | | (5) milky lotion preparation | |
|---|---|---|---|---|
| | | Mass % | (3) | (4) |
| | | Working Example 10 | 20 | 80 |

| Mass % | lipid *1 | arbutin aqueous solution *2 | deionized water | (4) |
|---|---|---|---|---|
| Comparative Example 10a | 2 | 6 | 12 | 80 |

| Mass % | | arbutin aqueous solution *2 | deionized water | (4) |
|---|---|---|---|---|
| Comparative Example 10b | | 6 | 14 | 80 |

| Mass % | | | arbutin | PBS(−) |
|---|---|---|---|---|
| Comparative Example 10c | | | 1 | 99 |
| Comparative Example 10d | | | | 100 |

*1 GDM-12
*2 arbutin (1 mass %) + deionized water (5 mass %)
*3 SDMAPA

<Preparing Method>

Working Example 10

The first step: at room temperature, adding an arbutin containing aqueous solution having a 6 mass % (arbutin having a 1 mass % and deionized water having a 5 mass %) to the GDM-12 having a 2 mass % and mixing them, so that a white viscous niosome suspension is obtained.

The second step: dissolving the SDMAPA having a 0.4 mass % completely in a 50% lactic-acid aqueous solution having a 0.6 mass % at a temperature of 70-80° C. and thereafter cooling it up to a room temperature of 30° C. or below, so that an SDMAPA aqueous solution is obtained.

The third step: adding the SDMAPA aqueous solution at the second step to the niosome suspension at the first step, stirring them softly so that a viscous solution is obtained, thereafter adding deionized water having a 7 mass % to it and stirring them softly, so that a viscous charged-niosome suspension is obtained.

The fourth step: at a temperature of 80° C., mixing deionized water having a 58.85 mass %, glycerol having a 6 mass %, diglycerol having a 6 mass %, diglycerol having a 1 mass %, 1,3-butylene glycol having a 4 mass %, 1,2-pentanediol having a 1 mass %, mannan having a 0.3 mass %, polyethylene glycol monostearate having a 1.4 mass %, glyceryl stearate having a 1.6 mass %, squalane having a 6 mass % and cetyl alcohol having a 1.5 mass %, emulsifying it and thereafter cooling it up to room temperature, so that a milky lotion is obtained.

The fifth step: adding the charged-niosome suspension obtained at the third step to the milky lotion obtained at the fourth step, so that a milky lotion preparation is obtained.

Comparative Example 10a

The first step: at room temperature, adding an arbutin containing aqueous solution having a 6 mass % (arbutin having a 1 mass % and deionized water having a 5 mass %) and deionized water having a 12 mass % to the GDM-12 having a 2 mass %, and stirring them softly, so that a niosome suspension is obtained.

The second step: adding the niosome suspension obtained at the first step to the milky lotion obtained in the same method as the fourth step of Working Example 10, so that a milky lotion preparation is obtained.

Comparative Example 10b

The first step: at room temperature, mixing an arbutin containing aqueous solution having a 6 mass % (arbutin having a 1 mass % and deionized water having a 5 mass %) and deionized water having a 14 mass %, so that an arbutin containing aqueous solution is obtained.

The second step: adding the arbutin containing aqueous solution obtained at the first step to the milky lotion obtained in the same method as the fourth step of Working Example 10, so that a milky lotion preparation is obtained.

Comparative Example 10c

At room temperature, arbutin having a 1 mass % and PBS (−) having a 99 mass % are mixed together, so that an arbutin PBS (−) aqueous solution is obtained.

Comparative Example 10d

PBS (−) itself is directly used.

<Results of the Percutaneous Absorption Tests>

Figure 9A:
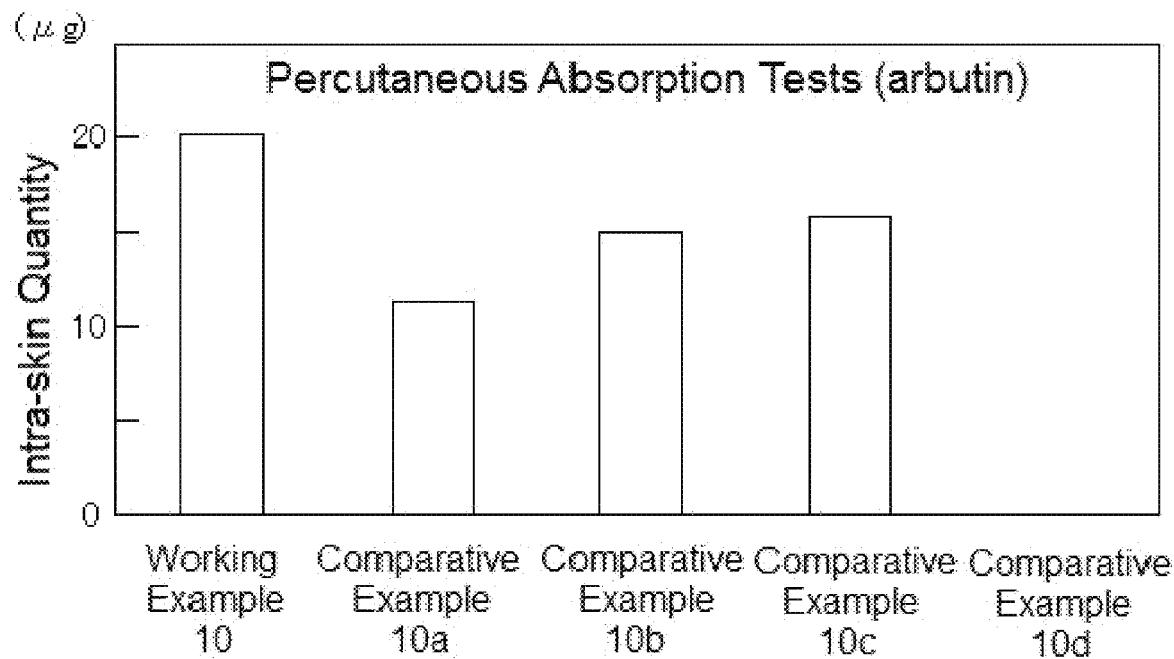
FIGS. 9A and 9B are graphical representations showing test results in Working Example 10 and Comparative Examples 10a, 10b, 10c and 10d.

FIG. 9A is a graphical representation showing test results for the percutaneous absorption in Working Example 10 and Comparative Examples 10a, 10b, 10c and 10d respectively. In Working Example 10, the storage in the skin is quite excellent, as compared with each comparative example.

<Results of the Skin-Whitening Effect Tests>

Figure 9B:
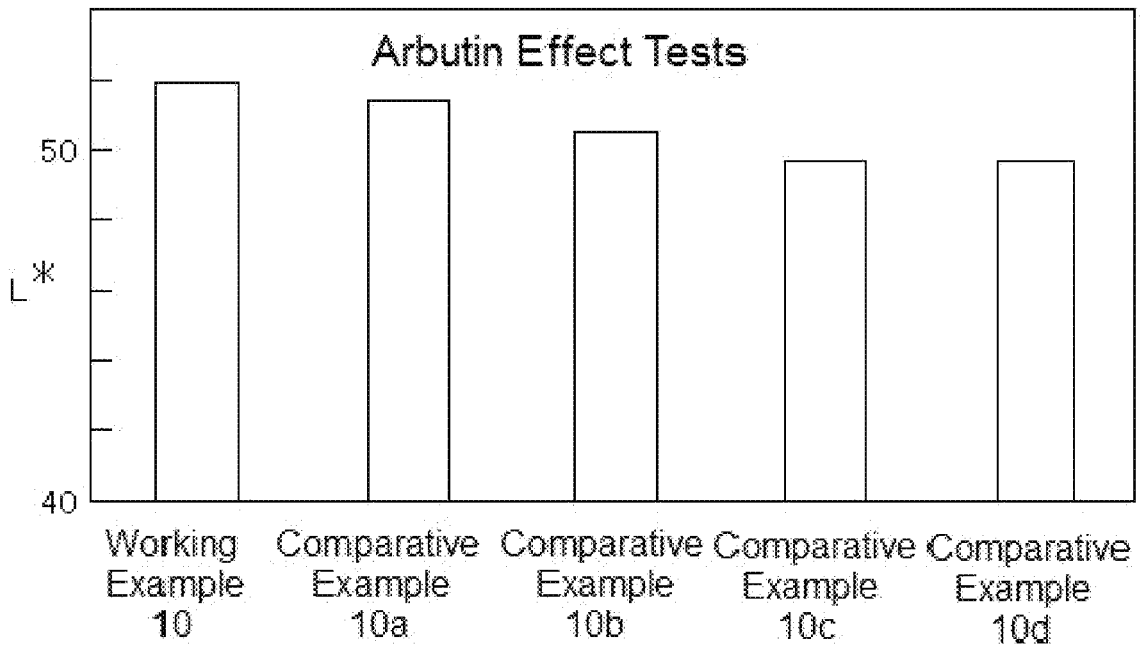

FIG. 9B is a graphical representation showing test results for the skin-whitening effect of arbutin as a skin-whitening agent by measuring the luminosity of cells in Working Example 10 and Comparative Examples 10a, 10b, 10c and 10d respectively. In Working Example 10, a greater skin-whitening effect is obtained than that of each comparative example. This is thought to result from the higher storability in the skin shown in FIG. 9(*a*).

(8) Other Working Examples

(8-1) Working Example 11

Table 11 shows an outline and constituent percentages of the preparing method in Working Example 11 where stearyltrimethyl ammonium chloride is used as the cationic surfactant. In Working Example 11, instead of the specified aqueous solution, deionized water is used, but this does not affect the formation of a charged niosome.

TABLE 11

| Mass % | (1)niosome suspension | | (2)cationic-surfactant aqueous solution | | | | (3)charged-niosome suspension | | |
|---|---|---|---|---|---|---|---|---|---|
| | lipid *1 | deionized water | cationic surfactant *2 | ethanol | citric acid | deionized water | (1) | (2) | deionized water |
| Working Example 11 | 2 | 5 | 0.4 | 0.5 | 0.1 | 4.3 | 7 | 5 | 88 |

*1 GDM-12
*2 stearyltrimethyl ammonium chloride

<Preparing Method>

The first step: at room temperature, adding deionized water having a 5 mass % to the GDM-12 having a 2 mass % and mixing them, so that a white viscous niosome suspension is obtained.

The second step: dissolving stearyltrimethyl ammonium chloride having a 0.4 mass %, ethanol having a 0.2 mass % and citric acid having a 0.1 mass % completely in deionized water having a 4.3 mass % at a temperature of 70-80° C. and thereafter cooling it up to a room temperature of 30° C. or below, so that a stearyltrimethyl-ammonium chloride aqueous solution is obtained.

The third step: adding the stearyltrimethyl-ammonium chloride aqueous solution at the second step to the niosome suspension at the first step, stirring them softly so that a viscous solution is obtained, thereafter adding deionized water having an 88 mass % to it and stirring them softly, so that a charged-niosome suspension is obtained.

(8-2) Working Example 12

Table 12 shows an outline and constituent percentages of the preparing method in Working Example 12 where diethylaminoethylamide stearate is used as the cationic surfactant.

TABLE 12

| Mass % | (1)niosome suspension | | (2)cationic-surfactant aqueous solution | | | (3)charged-niosome suspension | | |
|---|---|---|---|---|---|---|---|---|
| | lipid *1 | deionized water | cationic surfactant *2 | 50% lactic-acid aqueous solution | deionized water | (1) | (2) | deionized water |
| Working Example 12 | 2 | 5 | 0.4 | 0.6 | 4 | 7 | 5 | 88 |

*1 GDM-12
*2 diethylaminoethylamide stearate

<Preparing Method>

The first step: at room temperature, adding deionized water having a 5 mass % to the GDM-12 having a 2 mass % and mixing them, so that a white viscous niosome suspension is obtained.

The second step: dissolving diethylaminoethylamide stearate having a 0.4 mass %, a 50% lactic-acid aqueous solution having a 0.6 mass % and deionized water having a 4 mass % completely at a temperature of 70-80° C. and thereafter cooling it up to a room temperature of 30° C. or below, so that a diethylaminoethylamide stearate aqueous solution is obtained.

The third step: adding the diethylaminoethylamide stearate aqueous solution at the second step to the niosome suspension at the first step, stirring them softly so that a viscous solution is obtained, thereafter adding deionized water having an 88 mass % to it and stirring them softly, so that a charged-niosome suspension is obtained.

(8-3) Working Example 13

Table 13 shows an outline and constituent percentages of the preparing method in Working Example 13 where glycerol PEG distearate-23 (hereinafter, called the "GDS-23" for short) and cholesterol ester are used as the lipid.

TABLE 13

| Mass % | (1)niosome suspension | | | (2)cationic-surfactant aqueous solution | | | (3)charged-niosome suspension | | |
|---|---|---|---|---|---|---|---|---|---|
| | lipid *1 | cholesterol ester *2 | deionized water | cationic surfactant *3 | 50% lactic-acid aqueous solution | deionized water | (1) | (2) | deionized water |
| Working Example 13 | 2 | 1 | 5 | 0.4 | 0.6 | 4 | 8 | 5 | 87 |

*1 GDS-23
*2 macadamia-nut fatty-acid cholesteryl
*3 SDMAPA

<Preparing Method>

The first step: heating and dissolving the GDS-23 having a 2 mass % and macadamia-nut fatty-acid cholesteryl (Product name "YOFCO-MAC": by Nippon Fine Chemical Co.) having a 1 mass % at a temperature of 80° C., adding deionized water having a 5 mass % kept at a temperature of 80° C. to it, mixing them and thereafter cooling it up to a temperature of 45-50° C., so that a niosome suspension is obtained.

The second step: dissolving the SDMAPA having a 0.4 mass %, a 50% lactic-acid aqueous solution having a 0.6 mass % and deionized water having a 4 mass % completely at a temperature of 70-80° C. and thereafter cooling it up to a temperature of 50° C., so that an SDMAPA aqueous solution is obtained.

The third step: adding the SDMAPA aqueous solution at the second step to the niosome suspension at the first step at a temperature of 45-50° C., mixing them and thereafter cooling it up to a room temperature of 30° C. or below, then adding deionized water having an 87 mass % to it and mixing them, so that a charged-niosome suspension is obtained.

(8-4) Working Example 14

Table 14 shows an outline and constituent percentages of the preparing method in Working Example 14 where the GDS-23 and cholesterol ester are used as the lipid.

TABLE 14

| Mass % | (1)niosome suspension | | | (2)cationic-surfactant aqueous solution | | | (3)charged-niosome suspension | | |
|---|---|---|---|---|---|---|---|---|---|
| | lipid *1 | cholesterol ester *2 | calcein-Na containing aqueous solution *3 | cationic surfactant *4 | 50% lactic-acid aqueous solution | deionized water | (1) | (2) | deionized water |
| Working Example 14 | 1.79 | 0.7 | 5 | 0.4 | 0.6 | 4 | 7.49 | 5 | 87.51 |

*1 GDS-23
*2 macadamia-nut fatty-acid cholesteryl
*3 calcein Na (0.1 mass %) + deionized water (4.9 mass %)
*4 SDMAPA <Preparing Method>

The first step: heating and dissolving the GDS-23 having a 1.79 mass % and macadamia-nut fatty-acid cholesteryl (Product name "YOFCO-MAC": by Nippon Fine Chemical Co.) having a 0.7 mass % at a temperature of 80° C., adding a calcein-Na containing aqueous solution (calcein Na having a 0.1 mass % and deionized water having a 4.9 mass %) having a 5 mass % kept at a temperature of 80° C. to it and mixing them, so that a yellowish-brown viscous niosome suspension is obtained.

The second step: dissolving the SDMAPA having a 0.4 mass %, a 50% lactic-acid aqueous solution having a 0.6 mass % and deionized water having a 4 mass % completely at a temperature of 70-80° C. and thereafter cooling it up to a temperature of 50° C., so that an SDMAPA aqueous solution is obtained.

The third step: adding the SDMAPA aqueous solution at the second step to the niosome suspension at the first step, stirring them softly so that a yellowish-brown viscous solution is obtained, thereafter adding deionized water having an 87.51 mass % to it and stirring them softly, so that a charged-niosome suspension is obtained.

<Results of the Percutaneous Absorption Tests in Working Example 14>

Figure 10:
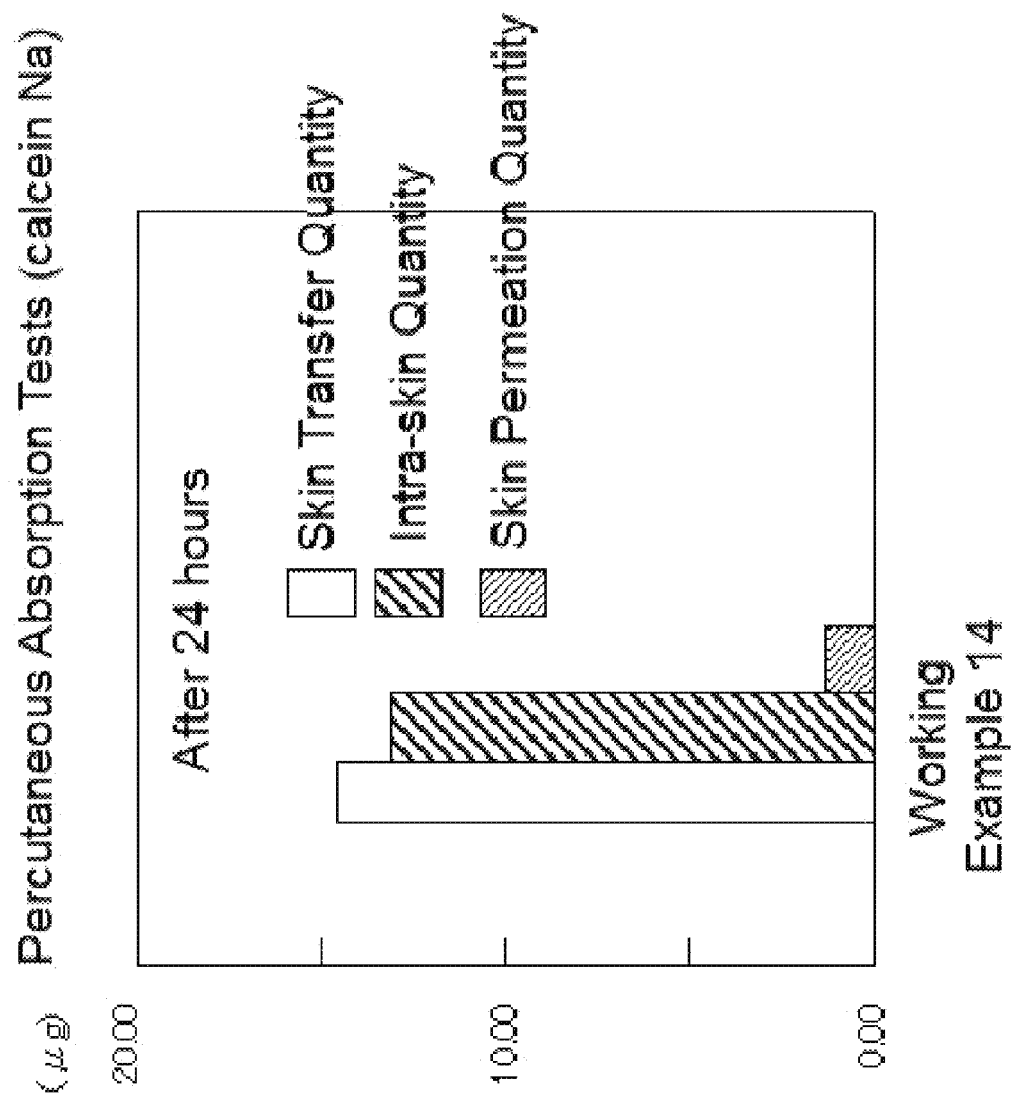
FIG. 10 is a graphical representation showing a test result of the percutaneous absorption in Working Example 14 under the same conditions as Working Examples 3 and 4 of FIG. 6.

FIG. 10 is a graphical representation showing a test result of the percutaneous absorption in Working Example 14 under the same conditions as Working Examples 3 and 4 of FIG. 6. As can be seen, the impregnation into the skin and the storage in the skin are quite excellent.

(8-5) Working Example 15

In Working Example 15, preparation is carried out using glycerol PEG distearate-12 (hereinafter, called the "GDS-12" for short) as the lipid, so that a charged-niosome suspension is obtained. The constituent percentages are identical to those of Working Example 1 even though the former differs in the kind of the lipid from the latter, and hence, a table of the constituents is omitted. In respect of the zeta potential, external appearance and optical microscope observation, the charged niosome of Working Example 15 is equivalent to the charged niosome of Working Example 1 (the same will also be below applied to the Working Examples 16-54).

<Preparing Method>

The first step: heating and dissolving the GDS-12 having a 2 mass % at a temperature of 50-60° C., adding deionized water having a 5 mass % kept at a temperature of 50-60° C. to it, mixing them and thereafter cooling it up to a temperature of 45-50° C., so that a niosome suspension is obtained.

The second step: dissolving the SDMAPA having a 0.4 mass %, a 50% lactic-acid aqueous solution having a 0.6 mass % and deionized water having a 4 mass % completely at a temperature of 70-80° C. and thereafter cooling it up to a temperature of 50° C., so that an SDMAPA aqueous solution is obtained.

The third step: adding the SDMAPA aqueous solution at the second step to the niosome suspension at the first step at a temperature of 45-50° C., mixing them and thereafter cooling it up to a room temperature of 30° C. or below, then adding deionized water having an 88 mass % to it and mixing them, so that a charged-niosome suspension is obtained.

(8-6) Working Example 16

In Working Example 16, preparation is carried out using glycerol PEG distearate-23 (hereinafter, called the "GDS-23" for short) as the lipid, so that a charged-niosome suspension is obtained. The constituent percentages are identical to those of Working Example 1 even though the former differs in the kind of the lipid from the latter, and hence, a table of the constituents is omitted.

<Preparing Method>

The first step: heating and dissolving the GDS-23 having a 2 mass % at a temperature of 50-60° C., adding deionized water having a 5 mass % kept at a temperature of 50-60° C. to it, mixing them and thereafter cooling it up to a temperature of 45-50° C., so that a niosome suspension is obtained.

The second step: dissolving the SDMAPA having a 0.4 mass %, a 50% lactic-acid aqueous solution having a 0.6 mass % and deionized water having a 4 mass % completely at a temperature of 70-80° C. and thereafter cooling it up to a temperature of 50° C., so that an SDMAPA aqueous solution is obtained.

The third step: adding the SDMAPA aqueous solution at the second step to the niosome suspension at the first step at a temperature of 45-50° C., mixing them and thereafter cooling it up to a room temperature of 30° C. or below, then adding deionized water having an 88 mass % to it and mixing them, so that a charged-niosome suspension is obtained.

(8-7) Working Examples 17-20

Table 15 shows an outline and constituent percentages of the preparing method in Working Examples 17-20 where the GDM-12 is used as the lipid and the SDMAPA is used as the cationic surfactant. In Working Examples 17-20, a different pH adjusting agent is used in each of the individual second steps.

TABLE 15

| | (1)niosome suspension | | (2)cationic-surfactant aqueous solution | | | | | | (3)charged-niosome suspension | | |
|---|---|---|---|---|---|---|---|---|---|---|---|
| | | | cationic | ph adjusting agent | | | | | | | |
| | | | | | pyrrolidone | | | | | | |
| Mass % | lipid *1 | deionized water | surfactant *2 | ascorbic acid | acetyl cysteine | calboxylic acid | glutamic acid | deionized water | (1) | (2) | deionized water |
| Working Example 17 | 2 | 5 | 0.4 | 0.4 | — | — | — | 4.2 | 7 | 5 | 88 |
| Working Example 18 | | | | — | 0.6 | — | — | 4 | | | |
| Working Example 19 | | | | — | — | 0.5 | — | 4.1 | | | |
| Working Example 20 | | | | — | — | — | 0.4 | 4.2 | | | |

*1 GDM-12
*2 SDMAPA

<Preparing Method>

The first step: at room temperature, adding deionized water having a 5 mass % to the GDM-12 having a 2 mass % and mixing them, so that a niosome suspension is obtained.

The second step: dissolving the SDMAPA having a 0.4 mass % and each pH adjusting agent having the corresponding mass % of Table 15 completely in deionized water having the corresponding mass % kept at a suitable temperature (80° C. in Working Example 20), and thereafter cooling it up to a room temperature of 30° C. or below (60° C. in Working Example 20), so that an SDMAPA aqueous solution is obtained.

The third step: in Working Examples 17-19, adding the cationic-surfactant aqueous solution at the second step to the niosome suspension at the first step (at 60° C. in Working Example 20), mixing them together, thereafter adding deionized water having an 88 mass % to it and mixing them (in Working Example 20, adding the deionized water to it and mixing them at a temperature of 40-50° C. and cooling it up to a room temperature of 30° C. or below), so that a charged-niosome suspension is obtained.

(8-8) Working Examples 21-24

Table 16 shows an outline and constituent percentages of the preparing method in Working Examples 21-24 where the GDM-12 is used as the lipid and diethylaminoethylamide stearate is used as the cationic surfactant. In Working Examples 21-24, a different pH adjusting agent is used in each of the individual second steps.

TABLE 16

| | (1)niosome suspension | | (2)cationic-surfactant aqueous solution | | | | | | (3)charged-niosome suspension | | |
|---|---|---|---|---|---|---|---|---|---|---|---|
| | | | cationic | ph adjusting agent | | | | | | | |
| | | | | | pyrrolidone | | | | | | |
| Mass % | lipid *1 | deionized water | surfactant *2 | ascorbic acid | acetyl cysteine | calboxylic acid | glutamic acid | deionized water | (1) | (2) | deionized water |
| Working Example 21 | 2 | 5 | 0.4 | 0.4 | — | — | — | 4.2 | 7 | 5 | 88 |
| Working Example 22 | | | | — | 0.6 | — | — | 4 | | | |
| Working Example 23 | | | | — | — | 0.5 | — | 4.1 | | | |
| Working Example 24 | | | | — | — | — | 0.4 | 4.2 | | | |

*1 GDM-12
*2 diethylaminoethylamide stearate

<Preparing Method>

The first step: the same as the first step of each of Working Examples 17-19.

The second step: dissolving diethylaminoethylamide stearate having a 0.4 mass % and each pH adjusting agent having the corresponding mass % of Table 16 completely in deionized water having the corresponding mass % kept at a suitable temperature (80° C. in Working Example 24), and thereafter cooling it up to a room temperature of 30° C. or below (60° C. in Working Example 24), so that a diethylaminoethylamide stearate aqueous solution is obtained.

The third step: in Working Examples 21-23, adding the cationic-surfactant aqueous solution at the second step to the niosome suspension at the first step (at 60° C. in Working Example 24), mixing them together, thereafter adding deionized water having an 88 mass % to it and mixing them (in Working Example 24, adding the deionized water to it and mixing them at a temperature of 40-50° C. and cooling it up to a room temperature of 30° C. or below), so that a charged-niosome suspension is obtained.

(8-9) Working Examples 25-28

Table 17 shows an outline and constituent percentages of the preparing method in Working Examples 25-28 where the GDM-12 is used as the lipid and cocoylarginineethyl PCA is used as the cationic surfactant. In Working Examples 25-28, a different pH adjusting agent is used in each of the individual second steps.

TABLE 17

| Mass % | (1) niosome suspension | | (2) cationic-surfactant aqueous solution | | | | | | (3) charged-niosome suspension | | |
|---|---|---|---|---|---|---|---|---|---|---|---|
| | | | cationic surfactant *2 | ph adjusting agent | | | | | | | |
| | lipid *1 | deionized water | | 50% lactic-acid aqueous solution | acetyl cysteine | pyrrolidone calboxylic acid | glutamic acid | deionized water | (1) | (2) | deionized water |
| Working Example 25 | 2 | 5 | 1 | 2 | — | — | — | 2 | 7 | 5 | 88 |
| Working Example 26 | | | | — | 0.5 | — | — | 3.5 | | | |
| Working Example 27 | | | | — | — | 1 | — | 3 | | | |
| Working Example 28 | | | | — | — | — | 0.5 | 3.5 | | | |

*1 GDM-12
*2 cocoylarginineethyl PCA

<Preparing Method>

The first step: the same as the first step of each of Working Examples 17-19.

The second step: dissolving cocoylarginineethyl PCA having a 1 mass % and each pH adjusting agent having the corresponding mass % of Table 17 completely in deionized water having the corresponding mass % kept at a suitable temperature (80° C. in Working Example 28), and thereafter cooling it up to a room temperature of 30° C. or below (60° C. in Working Example 28), so that a cocoylarginineethyl PCA aqueous solution is obtained.

The third step: in Working Examples 25-27, adding the cationic-surfactant aqueous solution at the second step to the niosome suspension at the first step (at 60° C. in Working Example 28), mixing them together, thereafter adding deionized water having an 88 mass % to it and mixing them (in Working Example 28, adding the deionized water to it and mixing them at a temperature of 40-50° C. and cooling it up to a room temperature of 30° C. or below), so that a charged-niosome suspension is obtained.

(8-10) Working Example 29

Table 18 shows an outline and constituent percentages of the preparing method in Working Example 29 where the GDM-12 is used as the lipid and palmitamidopropyltrimethyl ammonium chloride is used as the cationic surfactant.

TABLE 18

| Mass % | (1)niosome suspension | | (2)cationic-surfactant aqueous solution | | | (3)charged-niosome suspension | | |
|---|---|---|---|---|---|---|---|---|
| | lipid *1 | deionized water | cationic surfactant *2 | 50% lactic-acid aqueous solution | deionized water | (1) | (2) | deionized water |
| Working Example 29 | 2 | 5 | 0.9 | 1.2 | 2.9 | 7 | 5 | 88 |

*1 GDM-12
*2 palmitamidopropyltrimethyl ammonium chloride

<Preparing Method>

The first step: the same as the first step of each of Working Examples 17-19.

The second step: dissolving palmitamidopropyltrimethyl ammonium chloride having a 0.9 mass % and a 50% lactic-acid aqueous solution having a 1.2 mass % completely in deionized water having a 2.9 mass % kept at a suitable temperature, and thereafter cooling it up to a room temperature of 30° C. or below, so that a palmitamidopropyltrimethyl ammonium chloride aqueous solution is obtained.

The third step: adding the cationic-surfactant aqueous solution at the second step to the niosome suspension at the first step, mixing them together, thereafter adding deionized water having an 88 mass % to it and mixing them, so that a charged-niosome suspension is obtained.

(8-11) Working Example 30

Table 19 shows an outline and constituent percentages of the preparing method in Working Example 30 where the GDM-12 is used as the lipid and cetrimonium chloride is used as the cationic surfactant.

TABLE 19

| Mass % | (1)niosome suspension | | (2)cationic-surfactant aqueous solution | | | (3)charged-niosome suspension | | |
|---|---|---|---|---|---|---|---|---|
| | lipid *1 | deionized water | cationic surfactant *2 | 50% lactic-add aqueous solution | deionized water | (1) | (2) | deionized water |
| Working Example 30 | 2 | 5 | 0.4 | 0.6 | 4 | 7 | 5 | 88 |

*1 GDM-12
*2 cetrimonium chloride

<Preparing Method>

The first step: the same as the first step of each of Working Examples 17-19.

The second step: dissolving cetrimonium chloride having a 0.4 mass % and a 50% lactic-acid aqueous solution having a 0.6 mass % completely in deionized water having a 4 mass % kept at a suitable temperature, and thereafter cooling it up to a room temperature of 30° C. or below, so that a cetrimonium chloride aqueous solution is obtained.

The third step: adding the cationic-surfactant aqueous solution at the second step to the niosome suspension at the first step, mixing them together, thereafter adding deionized water having an 88 mass % to it and mixing them, so that a charged-niosome suspension is obtained.

(8-12) Working Examples 31 and 32

Table 20 shows an outline and constituent percentages of the preparing method in Working Examples 31 and 32 where the GDM-12 is used as the lipid and cetrimonium chloride is used as the cationic surfactant. In Working Examples 31 and 32, a different pH adjusting agent is used in each of the individual second steps. In the second steps, ethanol is used.

TABLE 20

| Mass % | (1)niosome suspension | | (2)cationic-surfactant aqueous solution | | | | | (3)charged-niosome suspension | | |
|---|---|---|---|---|---|---|---|---|---|---|
| | | | cationic | pH adjusting agent | | | | | | |
| | | | surfactant | 50% lactic-acid aqueous | ascorbic | | deionized | | | deionized |
| | lipid *1 | deionized water | *2 | solution | acid | ethanol | water | (1) | (2) | water |
| Working Example 31 | 2 | 5 | 0.4 | 0.6 | — | 0.3 | 3.7 | 7 | 5 | 88 |
| Working Example 32 | | | | — | 0.4 | | 3.9 | | | |

*1 GDM-12
*2 cetrimonium chloride

<Preparing Method>

The first step: the same as the first step of each of Working Examples 17-19.

The second step: dissolving cetrimonium chloride having a 0.4 mass % and each pH adjusting agent having the corresponding mass % of Table 20 completely in ethanol having a 0.3 mass % and deionized water having the corresponding mass % kept at a suitable temperature, and thereafter cooling it up to a room temperature of 30° C. or below, so that a cetrimonium chloride aqueous solution is obtained.

The third step: adding the cationic-surfactant aqueous solution at the second step to the niosome suspension at the first step, mixing them together, thereafter adding deionized water having an 88 mass % to it and mixing them, so that a charged-niosome suspension is obtained.

(8-13) Working Example 33

Table 21 shows an outline and constituent percentages of the preparing method in Working Example 33 where the GDM-12 is used as the lipid and behentrimonium chloride is used as the cationic surfactant.

TABLE 21

| Mass % | (1)niosome suspension | | (2)cationic-surfactant aqueous solution | | | | (3)charged-niosome suspension | | |
|---|---|---|---|---|---|---|---|---|---|
| | | | cationic | 50% lactic-acid | | | | | |
| | | | surfactant | aqueous | | deionized | | | deionized |
| | lipid *1 | deionized water | *2 | solution | ethanol | water | (1) | (2) | water |
| Working Example 33 | 2 | 5 | 0.4 | 0.8 | 0.1 | 3.7 | 7 | 5 | 88 |

*1 GDM-12
*2 behentrimonium chloride

<Preparing Method>

The first step: the same as the first step of each of Working Examples 17-19.

The second step: dissolving behentrimonium chloride having a 0.4 mass % and a 50% lactic-acid aqueous solution having a 0.8 mass % completely in ethanol having a 0.1 mass % and deionized water having a 3.7 mass % kept at a temperature of 80° C., and thereafter cooling it up to a room temperature of 30° C. or below, so that a behentrimonium chloride aqueous solution is obtained.

The third step: adding the cationic-surfactant aqueous solution at the second step to the niosome suspension at the first step at a temperature of 80° C., mixing them together, thereafter adding deionized water having an 88 mass % kept at a temperature of 60-70° C. to it and mixing them, so that a charged-niosome suspension is obtained.

(8-14) Working Example 34

Table 22 shows an outline and constituent percentages of the preparing method in Working Example 34 where the GDM-12 is used as the lipid and benzalkonium chloride is used as the cationic surfactant.

TABLE 22

| Mass % | (1)niosome suspension | | (2)cationic-surfactant aqueous solution | | | (3)charged-niosome suspension | | |
|---|---|---|---|---|---|---|---|---|
| | lipid *1 | deionized water | cationic surfactant *2 | 50% lactic-acid aqueous solution | deionized water | (1) | (2) | deionized water |
| Working Example 34 | 2 | 5 | 0.4 | 0.6 | 4 | 7 | 5 | 88 |

*1 GDM-12
*2 benzalkonium chloride

<Preparing Method>

The first step: the same as the first step of each of Working Examples 17-19.

The second step: dissolving benzalkonium chloride having a 0.4 mass % and a 50% lactic-acid aqueous solution having a 0.6 mass % completely in deionized water having a 4 mass % kept at a suitable temperature, and thereafter cooling it up to a room temperature of 30° C. or below, so that a benzalkonium chloride aqueous solution is obtained.

The third step: adding the cationic-surfactant aqueous solution at the second step to the niosome suspension at the first step, mixing them together, thereafter adding deionized water having an 88 mass % to it and mixing them, so that a charged-niosome suspension is obtained.

(8-15) Working Examples 35 and 36

Table 23 shows an outline and constituent percentages of the preparing method in Working Examples 35 and 36 where the GDM-12 is used as the lipid and ethyl sulfuric-acid lanolin fatty-acid aminopropylethyl dimethylanmonium (hereinafter, called the "quarternium-33") is used as the cationic surfactant. In Working Examples 35 and 36, a different pH adjusting agent is used in each of the individual second steps. In the second steps, DPG (dipropylene glycol) is used.

TABLE 23

| Mass % | (1)niosome suspension | | (2)cationic-surfactant aqueous solution | | | | | (3)charged-niosome suspension | | |
|---|---|---|---|---|---|---|---|---|---|---|
| | | | | pH adjusting agent | | | | | | |
| | | | cationic | 50% lactic-acid | | | | | | |
| | lipid *1 | deionized water | surfactant *2 | aqueous solution | ascorbic acid | DPG | deionized water | (1) | (2) | deionized water |
| Working Example 35 | 2 | 5 | 0.4 | 0.8 | — | 0.4 | 3.4 | 7 | 5 | 88 |
| Working Example 36 | | | | — | 0.4 | | 3.8 | | | |

*1 GDM-12
*2 quarternium-33

<Preparing Method>

The first step: the same as the first step of each of Working Examples 17-19.

The second step: dissolving the quarternium-33 having a 0.4 mass % and each pH adjusting agent having the corresponding mass % of Table 23 completely in DPG having a 0.4 mass % and deionized water having the corresponding mass % kept at a suitable temperature, and thereafter cooling it up to a room temperature of 30° C. or below, so that a quarternium-33 aqueous solution is obtained.

The third step: adding the cationic-surfactant aqueous solution at the second step to the niosome suspension at the first step, mixing them together, thereafter adding deionized water having an 88 mass % to it and mixing them, so that a charged-niosome suspension is obtained.

(8-16) Working Example 37

Table 24 shows an outline and constituent percentages of the preparing method in Working Example 37 where the GDS-12 is used as the lipid and cetrimonium chloride is used as the cationic surfactant.

TABLE 24

| Mass % | (1)niosome suspension | | (2)cationic-surfactant aqueous solution | | | | (3)charged-niosome suspension | | |
|---|---|---|---|---|---|---|---|---|---|
| | lipid *1 | deionized water | cationic surfactant *2 | 50% lactic-acid aqueous solution | ethanol | deionized water | (1) | (2) | deionized water |
| Working Example 37 | 2 | 5 | 0.4 | 0.8 | 0.3 | 3.5 | 7 | 5 | 88 |

*1 GDS-12
*2 cetrimonium chlorid

<Preparing Method>

The first step: dissolving the GDS-12 having a 2 mass % at a temperature of 45-55° C., adding deionized water having a 5 mass % kept at a temperature of 45-55° C. to it and mixing them, so that a niosome suspension is obtained.

The second step: dissolving cetrimonium chloride having a 0.4 mass %, a 50% lactic-acid aqueous solution having a 0.8 mass % and ethanol having a 0.3 mass % completely in deionized water having a 3.5 mass % kept at a suitable temperature, and thereafter warming it up to a temperature of 45-50° C., so that a cetrimonium chloride aqueous solution is obtained.

The third step: adding the cationic-surfactant aqueous solution at the second step to the niosome suspension at the first step at a temperature of 45-50° C., mixing them together, thereafter adding deionized water having an 88 mass % kept at a temperature of 45-50° C. to it and mixing them, and then, cooling it up to a room temperature of 30° C. or below, so that a charged-niosome suspension is obtained.

(8-17) Working Example 38

Table 25 shows an outline and constituent percentages of the preparing method in Working Example 38 where the GDS-12 is used as the lipid and the quarternium-33 is used as the cationic surfactant.

TABLE 25

| Mass % | (1)niosome suspension | | (2)cationic-surfactant aqueous solution | | | | | (3)charged-niosome suspension | | |
|---|---|---|---|---|---|---|---|---|---|---|
| | lipid *1 | deionized water | cationic surfactant *2 | 50% lactic-acid aqueous solution | DPG | deionized water | | (1) | (2) | deionized water |
| Working Example 38 | 2 | 5 | 0.4 | 0.8 | 0.4 | 3.4 | | 7 | 5 | 88 |

*1 GDS-12
*2 quarternium-33

<Preparing Method>
The first step: the same as the first step of Working Example 37.

The second step: dissolving the quarternium-33 having a 0.4 mass %, a 50% lactic-acid aqueous solution having a 0.8 mass % and DPG having a 0.4 mass % completely in deionized water having a 3.4 mass % kept at a suitable temperature, and thereafter warming it up to a temperature of 45-50° C., so that a quarternium-33 aqueous solution is obtained.

The third step: adding the cationic-surfactant aqueous solution at the second step to the niosome suspension at the first step at a temperature of 45-50° C., mixing them together, thereafter adding deionized water having an 88 mass % kept at a temperature of 45-50° C. to it and mixing them, and then, cooling it up to a room temperature of 30° C. or below, so that a charged-niosome suspension is obtained.

(8-18) Working Examples 39-42

Table 26 shows an outline and constituent percentages of the preparing method in Working Examples 39-42 where the GDS-23 is used as the lipid and cocoylarginineethyl PCA is used as the cationic surfactant. In Working Examples 39-42, a different pH adjusting agent is used in each of the individual second steps.

TABLE 26

| | (1)niosome suspension | | (2)cationic-surfactant aqueous solution | | | | | | (3)charged-niosome suspension | | |
|---|---|---|---|---|---|---|---|---|---|---|---|
| | | | cationic | 50% lactic-acid | pH adjusting agent | | | | | | |
| | | | | | pyrrolidone | | | | | | |
| Mass %, | lipid *1 | deionized water | surfactant *2 | aqueous solution | ascorbic acid | calboxylic acid | glutamic acid | deionized water | (1) | (2) | deionized water |
| Working Example 39 | 2 | 5 | 0.4 | 0.6 | — | — | — | 4 | 7 | 5 | 88 |
| Working Example 40 | | | | — | 0.4 | — | — | 4.2 | | | |
| Working Example 41 | | | | — | — | 0.5 | — | 4.1 | | | |
| Working Example 42 | | | | — | — | — | 0.3 | 4.3 | | | |

*1 GDS-23
*2 cocoylarginineethyl PCA

<Preparing Method>
The first step: dissolving the GDS-23 having a 2 mass % at a temperature of 45-55° C., adding deionized water having a 5 mass % kept at a temperature of 45-55° C. to it and mixing them, so that a niosome suspension kept at a temperature of 45-50° C. is obtained.

The second step: dissolving cocoylarginineethyl PCA having a 0.4 mass % and each pH adjusting agent having the corresponding mass % of Table 26 completely in deionized water having the corresponding mass % kept at a suitable temperature (80° C. in Working Example 42), and thereafter regulating it up to a temperature of 45-50° C. (cooling it up to a temperature of 60° C. in Working Example 42), so that a cocoylarginineethyl PCA aqueous solution is obtained.

The third step: adding the cationic-surfactant aqueous solution at the second step to the niosome suspension at the first step at a temperature of 45-50° C. (60° C. in Working Example 42), mixing them together, thereafter adding deionized water having an 88 mass % kept at a temperature of 45-50° C. to it and mixing them, and then, cooling it up to a room temperature of 30° C. or below, so that a charged-niosome suspension is obtained.

(8-19) Working Examples 43-45

Table 27 shows an outline and constituent percentages of the preparing method in Working Examples 43-45 where the GDS-23 is used as the lipid and dimethylaminopropylamide stearate (hereinafter, called the "amideamine MPS") is used as the cationic surfactant. In Working Examples 43-45, a different pH adjusting agent is used in each of the individual second steps.

TABLE 27

| Mass % | (1)niosome suspension | | (2)cationic-surfactant aqueous solution | | | | | (3)charged-niosome suspension | | |
|---|---|---|---|---|---|---|---|---|---|---|
| | | | cationic surfactant *2 | pH adjusting agent | | | | | | |
| | lipid *1 | deionized water | | ascorbic acid | glutamic acid | pyrrolidone calboxylic acid | deionized water | (1) | (2) | deionized water |
| Working Example 43 | 2 | 5 | 0.4 | 0.4 | — | — | 4.2 | 7 | 5 | 88 |
| Working Example 44 | | | | — | 0.3 | — | 4.3 | | | |
| Working Example 45 | | | | — | — | 0.3 | 4.3 | | | |

*1 GDS-23
*2 amideamine MPS

<Preparing Method>

The first step: the same as the first step of each of Working Examples 39-42.

The second step: dissolving the amideamine MPS having a 0.4 mass % and each pH adjusting agent having the corresponding mass % of Table 27 completely in deionized water having the corresponding mass % kept at a suitable temperature (80° C. in Working Example 44), and thereafter regulating it up to a temperature of 45-50° C. (cooling it up to a temperature of 60° C. in Working Example 44), so that an amideamine MPS aqueous solution is obtained.

The third step: adding the cationic-surfactant aqueous solution at the second step to the niosome suspension at the first step at a temperature of 45-50° C. (60° C. in Working Example 44), mixing them together, thereafter adding deionized water having an 88 mass % kept at a temperature of 45-50° C. to it and mixing them, and then, cooling it up to a room temperature of 30° C. or below, so that a charged-niosome suspension is obtained.

(8-20) Working Example 46

Table 28 shows an outline and constituent percentages of the preparing method in Working Example 46 where the GDS-23 is used as the lipid and palmitamidopropyltrimethyl ammonium chloride is used as the cationic surfactant.

TABLE 28

| Mass % | (1)niosome suspension | | (2)cationic-surfactant aqueous solution | | | (3)charged-niosome suspension | | |
|---|---|---|---|---|---|---|---|---|
| | lipid *1 | deionized water | cationic surfactant *2 | 50% lactic-acid aqueous solution | deionized water | (1) | (2) | deionized water |
| Working Example 46 | 2 | 5 | 0.4 | 0.8 | 3.8 | 7 | 5 | 88 |

*1 GDS-23
*2 palmitamidopropyitrimethyl ammonium chloride

<Preparing Method>

The first step: the same as the first step of each of Working Examples 39-42.

The second step: dissolving palmitamidopropyltrimethyl ammonium chloride having a 0.4 mass % and a 50% lactic-acid aqueous solution having a 0.8 mass % completely in deionized water having a 3.8 mass % kept at a suitable temperature, and thereafter regulating it up to a temperature of 45-50° C., so that a palmitamidopropyltrimethyl ammonium chloride aqueous solution is obtained.

The third step: adding the cationic-surfactant aqueous solution at the second step to the niosome suspension at the first step at a temperature of 45-50° C., mixing them together, thereafter adding deionized water having an 88 mass % kept at a temperature of 45-50° C. to it and mixing them, and then, cooling it up to a room temperature of 30° C. or below, so that a charged-niosome suspension is obtained.

(8-21) Working Examples 47-49

Table 29 shows an outline and constituent percentages of the preparing method in Working Examples 47-49 where the GDS-23 is used as the lipid and cetrimonium chloride is used as the cationic surfactant. In Working Examples 47-49, a different pH adjusting agent is used in each of the individual second steps. In the second steps, ethanol is used.

TABLE 29

| Mass % | (1) niosome suspension | | (2) cationic-surfactant aqueous solution | | | | | | (3) charged-niosome suspension | | |
|---|---|---|---|---|---|---|---|---|---|---|---|
| | | | cationic | pH adjusting agent | | | | | | | |
| | lipid *1 | deionized water | surfactant *2 | 50% lactic-acid aqueous solution | glutamic acid | ascorbic acid | ethanol | deionized water | (1) | (2) | deionized water |
| Working Example 47 | 2 | 5 | 0.4 | 0.6 | — | — | 7 | 3.7 | 7 | 5 | 88 |
| Working Example 48 | | | | — | 0.3 | — | | 4 | | | |
| Working Example 49 | | | | — | — | 0.4 | | 3.9 | | | |

*1 GDS + 23
*2 cetrimonium chloride

<Preparing Method>

The first step: the same as the first step of each of Working Examples 39-42.

The second step: dissolving cetrimonium chloride having a 0.4 mass % and each pH adjusting agent having the corresponding mass % of Table 29 completely in deionized water having the corresponding mass % kept at a suitable temperature (80° C. in Working Example 48), and thereafter regulating it up to a temperature of 45-50° C. (cooling it up to a temperature of 60° C. in Working Example 48), so that a cetrimonium chloride aqueous solution is obtained.

The third step: adding the cationic-surfactant aqueous solution at the second step to the niosome suspension at the first step at a temperature of 45-50° C. (60° C. in Working Example 48), mixing them together, thereafter adding deionized water having an 88 mass % kept at a temperature of 45-50° C. to it and mixing them, and then, cooling it up to a room temperature of 30° C. or below, so that a charged-niosome suspension is obtained.

(8-22) Working Example 50

Table 30 shows an outline and constituent percentages of the preparing method in Working Example 50 where the GDS-23 is used as the lipid and steartrimonium chloride is used as the cationic surfactant. In the second steps, ethanol is used.

TABLE 30

| Mass % | (1)niosome suspension | | (2)cationic-surfactant aqueous solution | | | | (3)charged-niosome suspension | | |
|---|---|---|---|---|---|---|---|---|---|
| | lipid *1 | deionized water | cationic surfactant *2 | 50% lactic-acid aqueous solution | ethanol | deionized water | (1) | (2) | deionized water |
| Working Example 50 | 2 | 5 | 0.4 | 0.6 | 0.3 | 3.7 | 7 | 5 | 88 |

*1 GDS-23
*2 steartrimonium chloride

<Preparing Method>

The first step: the same as the first step of each of Working Examples 39-42.

The second step: dissolving steartrimonium chloride having a 0.4 mass %, a 50% lactic-acid aqueous solution having a 0.6 mass % and ethanol having a 0.3 mass % completely in deionized water having a 3.7 mass % kept at a suitable temperature, and thereafter regulating it up to a temperature of 45-50° C., so that a steartrimonium chloride aqueous solution is obtained.

The third step: adding the cationic-surfactant aqueous solution at the second step to the niosome suspension at the first step at a temperature of 45-50° C., mixing them together, thereafter adding deionized water having an 88 mass % kept at a temperature of 45-50° C. to it and mixing them, and then, cooling it up to a room temperature of 30° C. or below, so that a charged-niosome suspension is obtained.

(8-23) Working Example 51

Table 31 shows an outline and constituent percentages of the preparing method in Working Example 51 where the GDS-23 is used as the lipid and behentrimonium chloride is used as the cationic surfactant. In the second steps, ethanol is used.

TABLE 31

| Mass % | (1)niosome suspension | | (2)cationic-surfactant aqueous solution | | | | (3)charged-niosome suspension | | |
|---|---|---|---|---|---|---|---|---|---|
| | lipid *1 | deionize water | cationic surfactant *2 | 50% lactic-acid aqueous solution | ethanol | deionized water | (1) | (2) | deionized water |
| Working Example 51 | 2 | 5 | 0.4 | 0.8 | 0.1 | 3.7 | 7 | 5 | 88 |

*1 GDS-23
*2 behentrimonium chloride

<Preparing Method>

The first step: the same as the first step of each of Working Examples 39-42.

The second step: dissolving behentrimonium chloride having a 0.4 mass %, a 50% lactic-acid aqueous solution having a 0.8 mass % and ethanol having a 0.1 mass % completely in deionized water having a 3.7 mass % kept at a suitable temperature, and thereafter regulating it up to a temperature of 45-50° C., so that a behentrimonium chloride aqueous solution is obtained.

The third step: adding the cationic-surfactant aqueous solution at the second step to the niosome suspension at the first step at a temperature of 45-50° C., mixing them together, thereafter adding deionized water having an 88 mass % kept at a temperature of 45-50° C. to it and mixing them, and then, cooling it up to a room temperature of 30° C. or below, so that a charged-niosome suspension is obtained.

(8-24) Working Example 52

Table 32 shows an outline and constituent percentages of the preparing method in Working Example 52 where the GDS-23 is used as the lipid and benzalkonium chloride is used as the cationic surfactant.

TABLE 32

| Mass % | (1)niosome suspension | | (2)cationic-surfactant aqueous solution | | | (3)charged-niosome suspension | | |
|---|---|---|---|---|---|---|---|---|
| | lipid *1 | deionized water | cationic surfactant *2 | 50% lactic-acid aqueous solution | deionized water | (1) | (2) | deionized water |
| Working Example 52 | 2 | 5 | 0.4 | 0.6 | 4 | 7 | 5 | 88 |

*1 GDS-23
*2 benzalkonium chloride

<Preparing Method>

The first step: the same as the first step of each of Working Examples 39-42.

The second step: dissolving benzalkonium chloride having a 0.4 mass % and a 50% lactic-acid aqueous solution having a 0.6 mass % completely in deionized water having a 4 mass % kept at a suitable temperature, and thereafter regulating it up to a temperature of 45-50° C., so that a benzalkonium chloride aqueous solution is obtained.

The third step: adding the cationic-surfactant aqueous solution at the second step to the niosome suspension at the first step at a temperature of 45-50° C., mixing them together, thereafter adding deionized water having an 88 mass % kept at a temperature of 45-50° C. to it and mixing them, and then, cooling it up to a room temperature of 30° C. or below, so that a charged-niosome suspension is obtained.

(8-25) Working Examples 53 and 54

Table 33 shows an outline and constituent percentages of the preparing method in Working Examples 53 and 54 where the GDS-23 is used as the lipid and the quarternium-33 is used as the cationic surfactant. In the second steps, DPG is used.

TABLE 33

| Mass % | (1)niosome suspension | | (2)cationic-surfactant aqueous solution | | | | | (3)charged-niosome suspension | | |
|---|---|---|---|---|---|---|---|---|---|---|
| | lipid *1 | deionized water | cationic surfactant *2 | 50% lactic-acid aqueous solution | glutamic acid | DPG | deionized water | (1) | (2) | deionized water |
| Working Example 53 | 2 | 5 | 0.4 | 0.8 | — | 0.4 | 3.4 | 7 | 5 | 88 |
| Working Example 54 | | | | — | 0.3 | | 3.9 | | | |

*1 GDS-23
*2 quarternium-3

<Preparing Method>

The first step: the same as the first step of each of Working Examples 39-42.

The second step: dissolving the quarternium-3 having a 0.4 mass %, each pH adjusting agent having the corresponding mass % of Table 33 and DPG having a 0.4 mass % completely in deionized water having the corresponding mass % kept at a suitable temperature (80° C. in Working Example 54), and thereafter regulating it up to a temperature of 45-50° C. (cooling it up to a temperature of 60° C. in Working Example 54), so that a quarternium-3 aqueous solution is obtained.

The third step: adding the cationic-surfactant aqueous solution at the second step to the niosome suspension at the first step at a temperature of 45-50° C. (60° C. in Working Example 54), mixing them together, thereafter adding deionized water having an 88 mass % kept at a temperature of 45-50° C. to it and mixing them, and then, cooling it up to a room temperature of 30° C. or below, so that a charged-niosome suspension is obtained.

As described above, the present invention has been described with reference to the working examples. However, the present invention is not limited to these working examples and includes any variations obvious from them.

DESCRIPTION OF THE SYMBOLS

1 glycerol skeletal part
2 hydrophilic part
3 hydrophobic part
4 hydrophilic part
5 hydrophobic part

The invention claimed is:

1. A preparing method for a positively electrified charged niosome, including the steps of:
    preparing a suspension of an uncharged niosome by mixing a lipid containing at least a diacylglycerol PEG adduct with water or an aqueous solution of an objective substance in the absence of a cationic surfactant and at a temperature where the lipid is in a liquid state so that the lipid forms the uncharged niosome spontaneously;
    separately preparing a cationic-surfactant aqueous solution by mixing a cationic surfactant with an acidic aqueous solution, the cationic surfactant being one or a plurality of cationic surfactants chosen from a group which consists of an aliphatic amine, an aliphatic or aliphatic-amide quaternary ammonium salt, an aliphatic amideamine and an acylamino acid derivative, the hydrophobic part of the cationic surfactant containing a saturated or unsaturated normal hydrocarbon group having a carbon number of 11 to 21, the acidic aqueous solution having a pH value equal to, or less than 4; and
    preparing a suspension of a charged niosome by mixing the suspension of the uncharged niosome with the separately prepared cationic-surfactant aqueous solution and allowing the cationic surfactant to modify a surface of the niosome with a positive charge of the hydrophilic part of the cationic surfactant whereby the niosomes within the suspension of charged niosomes have a substantially uniform particle size within the range of about 192 nm to about 232 nm, and wherein:
    the diacylglycerol PEG adduct is one or a plurality chosen from a group which consists of glycerol PEG dioleate-12, glycerol PEG dimyristate-12, glycerol PEG dipalmitate-23, glycerol PEG distearate-12 and glycerol PEG distearate-23;
    the aliphatic amine equivalent to the cationic surfactant is one or a plurality chosen from a group which consists of tetradecylamine, palmitylamine, stearylamine, oleylamine, linoleylamine, behenylamine, N,N-dimethyldodecylamine and N,N-dimethyl-n-octadecylamine;
    the aliphatic or aliphatic-amide quaternary ammonium salt equivalent to the cationic surfactant is one or a plurality chosen from a group which consists of tetradecyltrimethyl ammonium chloride, cetyltrimethyl ammonium chloride, stearyltrimethyl ammonium chloride, behenyltrimethyl ammonium chloride and palmitamidopropyltrimethyl ammonium chloride;
    the aliphatic amideamine equivalent to the cationic surfactant is one or a plurality chosen from a group which consists of diethylaminoethylamide myristate, dimethylaminoethylamide myristate, dimethylaminopropylamide myristate, dimethylaminopropylamide myristate, diethylaminoethylamide palmitate, dimethylaminoethylamide palmitate, dimethylaminopropylamide palmitate, diethylaminopropylamide palmitate, diethylaminoethylamide stearate, dimethylaminoethylamide stearate, dimethylaminopropylamide stearate, diethylaminopropylamide stearate, diethylaminoethylamide behenate, dimethylaminoethylamide behenate, dimethylaminopropylamide behenate and diethylaminopropylamide behenate; and
    the acylamino acid derivative equivalent to the cationic surfactant is a cocoylarginineethyl pyrrolidone carboxylate.

2. The positively-electrified charged niosome prepared by the method of claim 1.

3. The method of claim 1 and wherein the surface of the charged niosome has a zeta potential of at least 60 mV.

* * * * *